US006576787B1

(12) United States Patent
Nakano et al.

(10) Patent No.: US 6,576,787 B1
(45) Date of Patent: Jun. 10, 2003

(54) HYDROXYMETHYL-GROUP-CONTAINING ALICYCLIC COMPOUND AND PROCESS FOR PRODUCING THE SAME

(75) Inventors: Tatsuya Nakano, Himeji (JP); Hiroshi Shimojitosyo, Osaka (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/647,880

(22) PCT Filed: Feb. 1, 2000

(86) PCT No.: PCT/JP00/00529

§ 371 (c)(1),
(2), (4) Date: Oct. 6, 2000

(87) PCT Pub. No.: WO00/47541

PCT Pub. Date: Aug. 17, 2000

(30) Foreign Application Priority Data

Feb. 9, 1999 (JP) .............................................. 11-032041

(51) Int. Cl.$^7$ ......................... C07C 69/52; C07C 35/21; C07C 27/00
(52) U.S. Cl. ...................... 560/220; 562/129; 562/205; 568/816; 568/830
(58) Field of Search ................................ 568/816, 830; 562/205, 129

(56) References Cited

U.S. PATENT DOCUMENTS 5,621,019 A    4/1997   Nakano et al.

FOREIGN PATENT DOCUMENTS

WO    A1-9222518    12/1992

OTHER PUBLICATIONS

Panek et al, Tetrahedron Letters, 1987, vol. 28, No. 40 pp 4649–4652.*

House et al., Journal of Organic Chemistry, vol. 43, No. 11, pp. 2153–2157 (1978).

Kramer et al., Journal of Organic Chemistry, vol. 42, No. 17, pp. 2832–2836 (1977).

Greene et al., Journal of Organic Chemistry, vol. 32, No. 4, pp. 875–882 (1967).

Baddeley et al., Chemical Society Journal, pp. 4933–4936 (1965).

* cited by examiner

Primary Examiner—Alan L. Rotman
Assistant Examiner—Héctor M Reyes
(74) Attorney, Agent, or Firm—Birch, Stewart, Kolasch & Birch, LLP

(57) ABSTRACT

Hydroxymethyl-group-containing alicyclic compounds that are useful for making photosensitive resins and other functional polymers. Processes for producing the hydroxymethyl-group-containing alicyclic compounds. Polymerizable alicyclic compounds. The alicyclic moieties in all of these compounds may be a polycyclic ring such as a perhydroindene ring, a decalin ring, a perhydrofluorene ring, a perhydroanthracene ring, a perhydrophenanthrene ring, a tricyclo[5.2.1.0$^{2,6}$]decane ring, a perhydroacenaphthene ring, or a perhydrophenalene ring.

4 Claims, No Drawings

HYDROXYMETHYL-GROUP-CONTAINING ALICYCLIC COMPOUND AND PROCESS FOR PRODUCING THE SAME

This application is the national phase under 35 U.S.C. §371 PCT International Application No. PCT/JP00/00529 which has an Internation filing date of Feb. 1, 2000, which designated the Unites Stated of America.

TECHNICAL FIELD

The present invention relates to a novel hydroxymethyl-group-containing alicyclic compound which is useful as a monomer or a material thereof for photosensitive resins and other functional polymers, to a process for producing the same, and to a polymerizable alicyclic compound.

BACKGROUND ART

Alicyclic compounds each having a hydroxymethyl group are used as, for example, monomers or materials thereof for resist resins, and as intermediates of pharmaceuticals, and have received attention in recent years.

However, neither alicyclic compound nor ester of this compound with a carboxylic acid having a polymerizable unsaturated group is known, which alicyclic compound has a polycyclic carbon ring with two or three non-aromatic carbon rings each commonly possessing two carbon atoms and has a 1-(mono- or di-) substituted hydroxymethyl group combined with a carbon atom at a junction position between two rings.

DISCLOSURE OF INVENTION

Accordingly, it is an object of the present invention to provide an alicyclic compound having a polycyclic carbon ring with two or three non-aromatic carbon rings each commonly possessing two carbon atoms, and having a 1-(mono- or di-)substituted hydroxymethyl group combined with a carbon atom at a junction position between two rings, and to provide a process for producing the same.

Another object of the present invention is to provide an ester of the aforementioned alicyclic compound with a carboxylic acid having a polymerizable unsaturated group.

After intensive investigations to achieve the above objects, the present inventors found that a novel hydroxymethyl-group-containing alicyclic compound having an introduced specific substituent at a carbon atom adjacent to a hydroxyl group (α-position carbon atom) can be obtained by allowing an organometallic compound to act upon a polycyclic alicyclic compound having an acyl group, a carboxyl croup or a substituted oxycarbonyl group at a junction position. They further found that a novel polymerizable alicyclic compound can be obtained by allowing the aforementioned compound to react with a carboxylic acid having a polymerizable unsaturated group or a derivative thereof. The present invention has been accomplished based on these findings.

Specifically, the present invention provides a hydroxymethyl-group-containing alicyclic compound represented by the following formula (1) or (2):

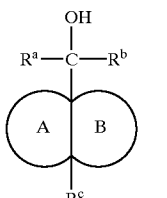

(1)

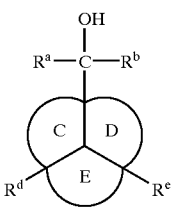

(2)

[wherein each of ring A, ring B, ring C, ring D, and ring E is a non-aromatic carbon ring; each of $R^a$ and $R^b$ is, identical to or different from each other, a hydrogen atom or a hydrocarbon group, and at least either of $R^a$ and $R^b$ is a hydrocarbon group; and each of $R^c$, $R^d$, and $R^e$ is a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a group represented by the following formula (3):

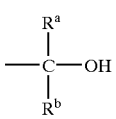

(3)

(wherein $R^a$ and $R^b$ have the same meanings as defined above.)]

In this compound, each of the ring A, ring B, ring C, ring D, and ring E may be a cyclopentane ring, a cyclohexane ring, or a bridged ring. Polycyclic carbon rings formed by the ring A and ring B or by the ring C, ring D and ring E in the formula (1) or (2) include, for example, a perhydroindene ring, a decalin ring, a perhydrofluorene ring, a perhydroanthracene ring, a perhydrophenanthrene ring, a tricyclo[5.2.1.0$^{2,6}$]decane ring, a perhydroacenaphthene ring, and a perhydrophenalene ring.

The present invention provides, in another aspect, a process for producing a hydroxymethyl-group-containing alicyclic compound (hereinafter simply referred to as "production process 1"). This process includes the step of allowing an acyl-group-containing alicyclic compound represented by the following formula (4) or (5):

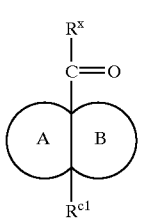

(4)

(5)

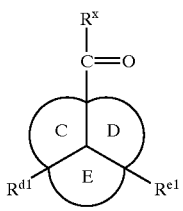

(wherein each of ring A, ring B, ring C, ring D, and ring E is a non-aromatic carbon ring; $R^x$ is a hydrogen atom or a hydrocarbon group; and each of $R^{c1}$, $R^{d1}$, and $R^{e1}$ is a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group) to react with an organometallic compound represented by the following formula (6):

 (6)

[wherein $R^y$ is a hydrogen atom or a hydrocarbon group, where $R^y$ is a hydrocarbon group when $R^x$ in the formula (4) or (5) is a hydrogen atom; and M is a metal atom which may have a ligand, or a group represented by the following formula (7):

 (7)

(wherein Y is a halogen atom)] to yield the compound represented by the formula (1) or (2).

In a further aspect, the present invention provides a process for producing a hydroxymethyl-group-containing alicyclic compound (hereinafter simply referred to as "production process 2"). This process includes the step of allowing an alicyclic carboxylic acid derivative represented by the following formula (8) or (9):

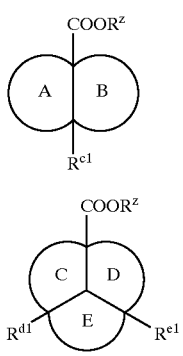

(wherein each of ring A, ring B, ring C, ring D, and ring E is a non-aromatic carbon ring; $R^z$ is a hydrogen atom or a hydrocarbon group which may have a substituent; and each of $R^{c1}$, $R^{d1}$, and $R^{e1}$ is a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, or an acyl group) to react with an organometallic compound represented by the following formula (6a):

 (6a)

[wherein $R^{a1}$ is a hydrocarbon group; and M is a metal atom which may have a ligand, or a group represented by the following formula (7):

 (7)

(wherein Y is a halogen atom)] to yield a compound represented by the following formula (1a) or (2a):

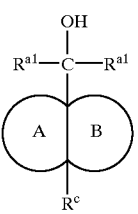

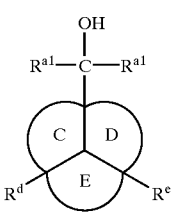

[wherein ring A, ring B, ring C, ring D, ring E and $R^{a1}$ have the same meanings as defined above; and each of $R^c$, $R^d$, and $R^e$ is a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a group represented by the following formula (3a):

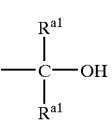 (3a)

(wherein $R^{a1}$ has the same meaning as defined above)].

In addition, the present invention provides a polymerizable alicyclic compound represented by the following formula (10) or (11):

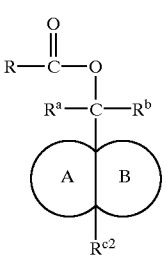 (10)

-continued

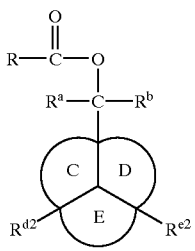
(11)

[wherein each of ring A, ring B, ring C, ring D, and ring E is a non-aromatic carbon ring; R is a polymerizable unsaturated group; each of $R^a$ and $R^b$ is, identical to or different from each other, a hydrogen atom or a hydrocarbon group, where at least either of $R^a$ and $R^b$ is a hydrocarbon group; and each of $R^{c2}$, $R^{d2}$, and $R^{e2}$ is a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a group represented by the following formula (12):

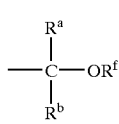
(12)

(wherein $R^f$ is a hydrogen atom or an RC(=O) group (where R has the same meaning as defined above); and $R^a$ and $R^b$ have the same meanings as defined above)].

In this compound, each of the ring A, ring B, ring C, ring D, and ring E may be a cyclopentane ring, a cyclohexane ring, or a bridged ring. Polycyclic carbon rings formed by the ring A and ring B, or by the ring C, ring D and ring E in the formula (10) or (11) include, for example, a perhydroindene ring, a decalin ring, a perhydrofluorene ring, a perhydroanthracene ring, a perhydrophenanthrene ring, a tricyclo[5.2.1.0$^{2,6}$]decane ring, a perhydroacenaphthene ring, and a perhydrophenalene ring. R includes, for example, a vinyl group, an isopropenyl group, and an allyl group.

In this connection, the term "group protected by a protective group" used in the present description means a group which can be derived from a group to be protected (a free functional group) and contains the major component of the group to be protected. The terms "acrylic" and "methacrylic" may be abbreviated to the term "(meth)acrylic", and the terms "acryloyl" and "methacryloyl" may be abbreviated to the term "(meth) acryloyl".

BEST MODE FOR CARRYING OUT THE INVENTION

[Hydroxymethyl-group-containing Alicyclic Compound]

In the present invention, each of the ring A, ring B, ring C, ring D, and ring E is a non-aromatic carbon ring. Such non-aromatic carbon rings include monocyclic or polycyclic rings (e.g., bridged rings) each having about 3 to 20 carbon atoms. The carbon rings may have a double bond as far as the rings are non-aromatic. If the carbon rings are polycyclic rings, the carbon rings may each have an aromatic ring, as far as a ring joined to an adjacent ring (the ring A, ring B, ring C, ring D or ring E) is a non-aromatic carbon ring.

Typical examples of the non-aromatic carbon rings include cyclopropane ring, cyclobutane ring, cyclopentane ring, cyclopentene ring, cyclohexane ring, cyclohexene ring, cycloheptane ring, cyclooctane ring, cyclodecane ring, cyclododecane ring, cyclopentadecane ring, and other monocyclic rings; perhydroindene ring, decalin ring, norbornane ring, norbornene ring, bicyclo[2.2.2]octane ring, and other bridged rings. Among these rings, for example, cyclopentane ring, cyclohexane ring, and bridged rings are preferred.

The non-aromatic carbon rings may have a substituent. Such substituents include, but are not limited to, halogen atoms (e.g., fluorine, chlorine, bromine, or iodine atom), alkyl groups (e.g., methyl, ethyl, isopropyl, and other $C_1$–$C_6$ alkyl groups, especially $C_1$–$C_4$ alkyl groups), cycloalkyl groups, aryl groups (e.g., phenyl group and naphthyl group), hydroxyl group, alkoxy groups (e.g., methoxy, ethoxy, isopropoxy, and other $C_1$–$C_6$ alkoxy groups, especially $C_1$–$C_4$ alkoxy groups), acyloxy groups (e.g., acetyloxy, propionyloxy group, (meth)acryloyloxy group, and other $C_2$–$C_4$ aliphatic acyloxy groups, especially $C_2$–$C_4$ aliphatic acyloxy groups), carboxyl group, alkoxycarbonyl groups (e.g., methoxycarbonyl, ethoxycarbonyl, propoxycarbonyl, and other $C_1$–$C_6$ alkoxycarbonyl groups, especially $C_1$–$C_4$ alkoxycarbonyl groups), substituted or unsubstituted carbamoyl groups (e.g., carbamoyl group; methylcarbamoyl, dimethylcarbamoyl, diethylcarbamoyl, and other mono- or di-$C_1$–$C_4$ alkyl-substituted carbamoyl groups), acyl groups (e.g., acetyl, propionyl, and other $C_2$–$C_6$ aliphatic acyl groups, especially $C_2$–$C_4$ aliphatic acyl groups), oxo group, substituted or unsubstituted amino groups (e.g., amino group; methylamino, ethylamino, propyl amino, dimethylamino, diethylamino, and other mono- or di-$C_1$–$C_6$ alkyl-substituted amino groups, especially mono- or di-$C_1$–$C_4$ alkyl-substituted amino groups), cyano group, and nitro group. The hydroxyl group, carboxyl group, and amino group may be protected by a conventional protective group.

In the formula (1), polycyclic carbon rings formed by the ring A and the ring B include, but are not limited to, perhydroindene ring, decalin ring, perhydrofluorene ring, perhydroanthracene ring, perhydrophenanthrene ring, and tricyclo[5.2.1.0$^{2,6}$]decane ring. In the formula (2), polycyclic carbon rings formed by the ring C, the ring D, and the ring E include, but are not limited to, perhydroacenaphthene ring and perhydrophenalene ring.

Hydrocarbon groups in $R^a$ and $R^b$ in the formulae (1) and (2) include, but are not limited to, methyl, ethyl, propyl, isopropyl, butyl, isobutyl, s-butyl, t-butyl, pentyl, isopentyl, 1-methylbutyl, 1-ethylpropyl, hexyl, isohexyl, 1-methylpentyl, 1-ethylbutyl, 1-methylhexyl, 1-ethylpentyl, 1-propylbutyl, octyl, isooctyl,1-methylheptyl, 1-ethylhexyl, 1-propylpentyl, nonyl, isononyl, 1-methyloctyl, decyl, 1-methylnonyl, tetradecyl, hexadecyl, octadecyl, allyl, propenyl, and other straight- or branched-chain aliphatic hydrocarbon groups (alkyl groups, alkenyl group, and alkynyl groups) each having about 1 to 20 (preferably 1 to 10, and particularly 1 to 6) carbon atoms; cyclopropyl, cyclobutyl, cyclopentyl, cyclohexyl, cyclohexenyl, cyclooctyl, and other alicyclic hydrocarbon groups (cycloalkyl groups and cycloalkenyl groups) each having about 3 to 8 carbon atoms; phenyl, naphthyl, and other aromatic hydrocarbon groups (aryl groups) each having about 6 to 14 carbon atoms. These hydrocarbon groups may have a substituent.

Preferred $R^a$ and $R^b$ include, for example, hydrogen atom, alkyl groups each having about 1 to 10 (particularly 1 to 6) carbon atoms, and cycloalkyl groups each having 3 to 8 members. Among them, typically preferred $R^a$ and $R^b$ include, for example, methyl, ethyl, propyl, isopropyl, butyl, s-butyl, 1-methylbutyl, 1-ethylpropyl group, pentyl group, and other alkyl groups each having about 1 to 5 carbon atoms; and cyclopropyl, cyclobutyl, cyclopentyl, cyclohexyl group, and other cycloalkyl groups each having 3 to 8 members. Each of $R^a$ and $R^b$ is a hydrogen atom or an alkyl group having about 1 to 4 carbon atoms, and is especially methyl group or ethyl group in many cases.

The halogen atoms in $R^c$, $R^d$, and $R^e$ include, but are not limited to, fluorine, chlorine, and bromine atoms. The alkyl group includes, for example, methyl, ethyl, propyl, isopropyl, butyl, isobutyl, s-butyl, t-butyl, pentyl, hexyl, octyl, decyl, and other alkyl groups each having about 1 to 10 carbon atoms, preferably having about 1 to 6 carbon atoms, and more preferably having about 1 to 4 carbon atoms. Especially preferred alkyl groups are methyl group and ethyl group, of which methyl group is typically preferred.

The protective groups for hydroxyl group and hydroxymethyl group in $R^c$, $R^d$, and $R^e$ include conventional protective groups. Such protective groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, and 2,2,2-trichloroethyl groups), tetrahydropyranyl group, tetrahydrofuranyl group, acyl groups (e.g., formyl, acetyl, propionyl, butyryl, isobutyryl, valeryl, pivaloyl, and other $C_1$–$C_6$ aliphatic acyl groups; acetoacetyl group; benzoyl, naphthoyl, and other aromatic acyl groups), alkoxycarbonyl groups (e.g., methoxycarbonyl, ethoxycarbonyl, t-butoxycarbonyl, and other $C_1$–$C_4$-alkoxycarbonyl groups), aralkyloxycarbonyl groups (e.g., benzyloxycarbonyl group and p-methoxybenzyloxycarbonyl group), substituted or unsubstituted carbamoyl groups (e.g., carbamoyl, methylcarbamoyl, and phenylcarbamoyl groups), dialkylphosphinothioyl groups (e.g., dimethylphosphinothioyl group), diarylphosphinothioyl groups (e.g., diphenylphosphinothioyl group), and substituted silyl groups (e.g., trimethylsilyl, t-butyldimethylsilyl, tribenzylsilyl, and triphenylsilyl groups). When the molecule to be protected has two or more hydroxyl groups (inclusive of hydroxymethyl groups), the protective groups also include divalent hydrocarbon groups (e.g., methylene, ethylidene, isopropylidene, cyclopentylidene, cyclohexylidene, and benzylidene groups) which may have a substituent. Preferred protective groups for hydroxyl group include, for example, $C_1$–$C_4$ alkyl groups; substituted methyl groups, substituted ethyl groups, acyl groups, $C_1$–$C_4$ alkoxy-carbonyl groups, substituted or unsubstituted carbamoyl groups, and divalent hydrocarbon groups which may have a substituent.

Protective groups for amino group in $R^c$, $R^d$, and $R^e$ include the aforementioned alkyl groups, aralkyl groups, acyl groups, alkoxycarbonyl groups, aralkyloxycarbonyl groups, dialkylphosphinothioyl groups, and diarylphoshinothioyl groups mentioned as the protective groups for hydroxyl group. Preferred protective groups for amino group are, for example, $C_1$–$C_4$ alkyl groups, $C_1$–$C_6$ aliphatic acyl groups, aromatic acyl groups, and $C_1$–$C_4$ alkoxycarbonyl groups.

Illustrative protective groups for carboxyl group in $R^c$, $R^d$, and $R^e$ include, but are not limited to, alkoxy groups (e.g., methoxy, ethoxy, butoxy, and other $C_1$–$C_6$ alkoxy groups) cycloalkyloxy groups, aryloxy groups (e.g., phenoxy group), aralkyloxy groups (e.g., benzyloxy group), trialkylsllyloxy groups (e.g., trimethylsilyloxygroup), amino groups which may have a substituent (e.g., amino group; methylamino group, dimethylamino group, and other mono- or di-$C_1$–$C_6$ alkylamino groups), hydrazino group, alkoxycarbonylhydrazino groups, and aralkyloxycarbonylhydrazino groups. Preferred protective groups for carboxyl group are $C_1$–$C_6$ alkoxy groups (especially, $C_1$–$C_4$ alkoxy groups), and mono- or di-$C_1$–$C_6$ alkylamino groups (especially, mono- or di-$C_1$–$C_4$ alkylamino groups).

The acyl groups in $R^c$, $R^d$, and $R^e$ include, but are not limited to, $C_2$–$C_5$ saturated aliphatic acyl groups (e.g., acetyl, propionyl, and butyryl groups), cycloalkylcarbonyl groups (e.g., cyclopentylcarbonyl, and cyclohexylcarbonyl groups), and arylcarbonyl groups (e.g., benzoyl group). Among them, acetyl group and propionyl group are preferred, of which acetyl group is typically preferred.

$R^a$ and $R^b$ in the group represented by the formula (3) are the same as $R^a$ and $R^b$ in the formulae (1) and (2).

Preferred $R^c$, $R^d$, and $R^e$ include, for example, hydrogen atom, $C_1$–$C_4$ alkyl groups, hydroxyl group which may be protected by a protective group, the group represented by the formula (3), and carboxyl group which may be protected by a protective group.

Typical examples of the hydroxymethyl-group-containing alicyclic compounds include, but not limited to, α,α-dimethyl-3a-perhydroindenemethanol, α,α-dimethyl-7a-hydroxy-3a-perhydroindenemethanol; α,α-dimethyl-4a-decalinmethanol, α,α-dimethyl-8a-hydroxy-4a-decalinmethanol, α,α-dimethyl-8a-)1-hydroxy-1-methylethyl)-4a-decalinmethanol, α,α-dimethyl-8a-(2-methoxyethoxymethoxy)-4a-decalinmethanol, α,α-dimethyl-8a-methoxymethoxy-4a-decalinmethanol, α,α-dimethyl-8a-methylthiomethoxy-4a-decalinmethanol, α,α-dimethyl-8a-[2-(trimethylsilyl)ethoxymethoxy]-4a-decalinmethanol, α,α-dimethyl-8a-methoxy-4a-decalinmethanol, 8a-acetyloxy-α,α-dimethyl-4a-decalinmethanol, 8a-acetoacetyloxy-α,α-dimethyl-4a-decalinmethanol, α-ethyl-α-methyl-4a-decalinmethanol, α-ethyl-8a-hydroxy-α-methyl-4a-decalinmethanol, α-isopropyl-α-methyl-4a-decalinmethanol, α-isopropyl-8a-hydroxy-α-methyl-4a-decalinmethanol, α,α-diethyl-4a-decalinmethanol, α,α-diethyl-8a-hydroxy-4a-decalinmethanol; α,α-dimethyl-4a-perhydrofluorenemethanol, α,α-dimethyl-9a-perhydrofluorenemethanol, α,α-dimethyl-9a-hydroxy-4a-perhydrofluorenemethanol, α,α-dimethyl-4a-hydroxy-9a-perhydrofluorenemethanol; α,α-dimethyl-4a-perhydroanthracenemethanol, α,α-dimethyl-9a-hydroxy-4a-perhydroanthracenemethanol, α,α-dimethyl-9a-(1-hydroxy-1-methylethyl)-4a-perhydroanthracenemethanol, α,α-dimethyl-9a-(2-methoxyethoxymethoxy)-4a-perhydroanthracenemethanol, α,α-dimethyl-9a-methoxymethoxy-4a-perhydroanthracenemethanol, α,α-dimethyl-9a-methylthiomethoxy-4a-perhydroanthracenemethanol, α,α-dimethyl-9a-[2-(trimethylsilyl)ethoxymethoxy]-4a-perhydroanthracenemethanol, α,α-dimethyl-9a-methoxy-4a-perhydroanthracenemethanol, 9a-acetyloxy-α,α-dimethyl-4a-perhydroanthracenemethanol, 9a-acetoacetyloxy-α,α-dimethyl-4a-perhydroanthracenemethanol, α-ethyl-α-methyl-4a-perhydroanthracenemethanol, α-ethyl-9a-hydroxy-α-methyl-4a-perhydroanthracenemethanol, α-isopropyl-α-methyl-4a-perhydroanthracenemethanol, α-isopropyl-9a-hydroxy-α-methyl-4a-perhydroanthracenemethanol, α,α-diethyl-4a-perhydroanthracenemethanol, α,α-diethyl-9a-hydroxy-4a-perhydroanthracenemethanol; α,α-dimethyl-10a-perhydrophenanthrenemethanol, α,α-dimethyl-4a-hydroxy-10a-perhydrophenanthrenemethanol, α,α-dimethyl-8a-hydroxy-10a-perhydrophenanthrehemethanol; α,α-dimethyl-2-tricyclo[5.2.1.0$^{2,6}$]decanemethanol, α,α-dimethyl-6-hydroxy-2-tricyclo[5.2.1.0$^{2,6}$]decanemethanol, α,α-dimethyl-6-)1-hydroxy-1-methylethyl)-2-tricyclo[5.2.1.0$^{2,6}$]decanemethanol, α,α-dimethyl-6-(2-methoxyethoxymethyl)-2-tricyclo[5.2.1.0$^{2,6}$]decanemethanol, α,α-dimethyl-6-methoxymethoxy-2-tricyclo[5.2.1.0$^{2,6}$]decanemethanol, α,α-dimethyl-6-methylthiomethoxy-2-tricyclic[5.2.1.0$^{2,6}$]decanemethanol, α,α-dimethyl-6-[2-(trimethylsilyl)ethoxymethoxy]-2-tricyclo[5.2.1.0$^{2,6}$]decanemethanol, α,α-dimethyl-6-methoxy-2-tricyclo[5.2.1.0$^{2,6}$]decanemethanol, 6-acetyloxy-α,α-dimethyl-2-tricyclo[5.2.1.0$^{2,6}$]decanemethanol, 6-acetoacetyloxy-α,α-dimethyl-2-tricyclo[5.2.1.0$^{2,6}$]decanemethanol, α-ethyl-α-methyl-2-tricyclo[5.2.1.0$^{2,6}$]decanemethanol, α-ethyl-6-hydroxy-α-methyl-2-tricyclo[5.2.1.0$^{2,6}$]decanemethanol, α-isopropyl-α-methyl-2-tricyclo[5.2.1.0$^{2,6}$]decanemethanol, α-isopropyl-6-hydroxy-α-methyl-2-tricyclo[5.2.1.0$^{2,6}$]decanemethanol, α,α-diethyl-2-tricyclo[5.2.1.0$^{2,6}$]decanemethanol, α,α-diethyl-6-hydroxy-2-tricyclo[5.2.1.0 $^{2,6}$]decanemethanol; α,α-dimethyl-2a-perhydroacenaphthenemethanol, α,α-dimethyl-8a-hydroxy-2a-perhydroacenaphthenemethanol; α,α-dimethyl-3a-perhydrophenalenemethanol, and α,α-dimethyl-6a-hydroxy-3a-perhydrophenalenemethanol.

When the invented hydroxymethyl-group-containing alicyclic compounds are converted into esters of, for example, carboxylic acids such as acrylic acid (e.g., the invented polymerizable alicyclic compounds), the esters themselves are insoluble in alkalis but are very easily decomposed by acids to yield alkali-soluble carboxylic acids. Accordingly, the aforementioned compounds can be used as monomers or materials thereof for resist resins.

Of these compounds, when a compound having a hydroxyl group protected by a protective group and bonded at the junction position of rings or another position is converted into an ester of a carboxylic acid (e.g., acrylic acid) as mentioned above to yield a polymer, the resulting polymer has a long list of advantages such as: (i) hydrophilicity, adhesion to substrates, and other characteristics of the polymer can be improved and controlled by appropriately selecting the protective group, (ii) occurrence of side reactions upon polymerization can be suppressed, and the molecular weight can be easily controlled and handling property can be improved, as compared with, for example, a compound having a free hydroxyl group combined at the position, and (iii) the protected hydroxyl group can be converted into a free hydroxyl group through deprotection where necessary. Accordingly, the compound in question is useful as a monomer or a material thereof for resist resins and other highly functional polymers.

A compound having a hydroxyl group, hydroxymethyl group, carboxyl group, or another functional group on its ring can serve to further improve the functions or to add or control a variety of functions. In addition, the invented compounds can be used as, for example, intermediates of pharmaceuticals and the like.

[Production Process of Hydroxymethyl-group-containing Alicyclic Compound (Production Process 1)]

In the invented production process 1, hydrocarbon groups in $R^x$ and $R^y$ in the formula (4), formula (5), and formula (6) are similar to the hydrocarbon groups in $R^a$ and $R^b$ in the formula (1) and formula (2). Halogen atoms, alkyl groups, protective groups for hydroxyl group, protective groups for hydroxymethyl group, protective groups for amino group, protective groups for carboxyl group, and acyl groups in $R^{c1}$, $R^{d1}$, and $R^{e1}$ include, for example, the corresponding substituents exemplified in the $R^c$, $R^d$, and $R^e$.

In the formula (6), metal atoms in M include, but are not limited to, lithium and other alkali metal atoms, and cerium, titanium, copper, and other transition metal atoms. These metal atoms may have a ligand. The term "ligand" as used in the present description also means and includes atoms or atomic groups corresponding to cations in ate-complexes. Such ligands include, for example, chlorine atom and other halogen atoms, isopropoxy group and other alkoxy groups, diethylamino group and other dialkylamino groups, cyano group, alkyl groups, lithium atom and other alkali metal atoms (as cations in ate-complexes). In the formula (7), halogen atoms represented by Y include chlorine, bromine, and iodine atoms. Typical examples of the organometallic compounds represented by the formula (6) include, but are not limited to, dimehyldiisopropoxytitanium and other oraganotitanium compounds (e.g., ate-complexes of organic titanium), organomagnesium compounds (e.g., Grignard reagents), and organolithium compounds.

The proportion of the compound represented by the formula (6) is, for example, about 0.7 to 3 moles, and preferably about 0.9 to 1.5 moles, relative to 1 mole of the acyl-group-containing alicyclic compound represented by the formula (4) or (5).

The invented process is usually performed in an organic solvent. Such organic solvents have only to be solvents inert in a reaction, and include, for example, diethyl ether, 1,2-dimethoxyethane, tetrahydrofuran, and other ethers; and heptane, hexane, octane, and other aliphatic hydrocarbons.

A reaction temperature can be appropriately selected within a range of, for example, −100° C. to 150° C. depending on the types of reactants. For example, when M in the compound represented by the formula (6) is a metal atom (e.g., lithium), the reaction temperature is, for example, about −100° C. to 20° C. When a compound in which M is the group represented by the formula (7) is used as the compound represented by the formula (6), the reaction temperature is, for example, about 0° C. to 150° C., and preferably about 20° C. to 100° C.

A reaction can be performed in a batch system, semi-batch system, continuous system or another conventional system. After the completion of the reaction, a target reaction product can be usually obtained by adding an aqueous solution containing an acid (e.g., hydrochloric acid) or a salt (e.g., ammonium chloride) to a reaction mixture for quenching, adjusting the acidity or alkalinity of the resulting mixture according to necessity, and subjecting the resulting mixture to a conventional separation and purification means such as filtration, concentration, extraction, distillation, crystallization, recrystallization, and column chromatography.

The compounds represented by the formula (6) can be prepared according to a conventional technique. For example, a compound where M in the formula (6) is the group represented by the formula (7) can be prepared by applying a conventional process for obtaining a Grignard reagent. Specifically, this compound can be prepared by adding a small amount of iodine, ethyl bromide, or another reaction accelerator to a mixture containing metal magnesium, a portion of a compound represented by the following formula (13):

$$R^y—Y \quad (13)$$

(wherein $R^y$ and Y have the same meanings as defined above) and an organic solvent to initiate a reaction, and adding the remainder of the compound represented by the formula (13) to the mixture to continue the reaction. As the organic solvent, the solvents used in the invented process can be employed. The proportion of the metal magnesium is, for example, about 1 to 1.5 moles relative to 1 mole of the compound represented by the formula (13). A reaction temperature is, for example, about 0° C. to 100° C. The compounds represented by the formula (6) thus obtained can be used in the invented process without isolation.

The invented process can produce the novel hydroxymethyl-group-containing alicyclic compound in a good yield with a simple and easy operation. When the acyl-group-containing alicyclic compound represented by the formula (4) or (5) has plural acyl groups [$R^xCO$ groups] in the molecule, a hydroxymethyl-group-containing alicyclic compound having plurality of the groups represented by the formula (3) can be obtained by selecting reaction conditions (e.g., by increasing the proportion of the compound represented by the formula (6)).

[Preparation of Acyl-group-containing Alicyclic Compound Represented by the Formula (4) or (5)]

The acyl-group-containing compound represented by the formula (4) or (5) for use as a material in the invented production process 1 can be obtained, for example, by allowing a compound represented by the following formula (14) or (15):

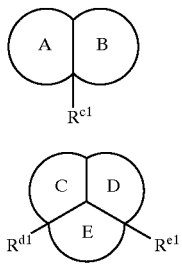

(wherein ring A, ring B, ring C, ring D, ring E, $R^{c1}$, $R^{d1}$, and $R^{e1}$ have the same meaning as defined above) to react with an acylating agent composed of (A) a 1,2-dicarbonyl compound represented by the following formula (16):

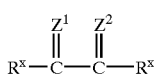

(wherein each of $Z^1$ and $Z^2$ is, identical to or different from each other, an oxygen atom or a hydroxyl group; and $R^x$ has the same meaning as defined above) or a hydroxy reductant thereof, (B) oxygen, and (C) at least one compound selected from (C1) a metallic compound and (C2) an imide compound represented by the following formula (17):

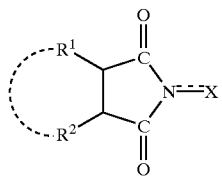

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group; and one or two of N-substituted cyclic imido group indicated in the formula (17) may be further formed on the $R^1$, $R^2$, or on the double bond or aromatic or non-aromatic ring formed together by $R^1$ and $R^2$).

Each of the aforementioned $Z^1$ and $Z^2$ is an oxygen atom or a hydroxyl group, and a bond between a carbon atom and $Z^1$ or $Z^2$ is a single bond or a double bond.

Typical examples of the 1,2-dicarbonyl compound are biacetyl (2,3-butanedione), 2,3-pentanedione, 3,4-hexanedione, bibenzoyl (benzil), acetylbenzoyl, and other α-diketones. Typical examples of the hydroxy reductant of the 1,2-dicarbonyl compound are acetoin, benzoin, and other α-keto-alcohols; and 2,3-butanediol, 2,3-pentanediol, and other vicinal diols.

As the oxygen (B), either of molecular oxygen and active oxygen can be used. Such molecular oxygen includes, but is not limited to, pure oxygen, and oxygen diluted with an inert gas such as nitrogen, helium, argon or carbon dioxide, or air. The molecular oxygen is often used as the oxygen (B).

Metallic elements constituting the metallic compounds (C1) are not critical and can be any of metallic elements of the Groups 1 to 15 of the Periodic Table of Elements. The term "metallic element" as used in the present description also includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), and Group 15 elements (e.g., Sb, Bi). Preferred metallic elements include transition metal elements (elements of Groups 3 to 12 of the Periodic Table of Elements). Among them, elements of the Groups 5 to 11, especially elements of Groups 5 and 9 of the Periodic Table of Elements are preferred, of which Co and V are typically preferred. The valency of the metallic element is not critical, and is about 0 to 6 in many cases.

The metallic compounds (C1) include, but are not limited to, elementary substances, hydroxides, oxides (including complex oxides), halides (fluorides, chlorides, bromides, and iodides), salts of oxoacids (e.g., nitrates, sulfates, phosphates, borates, and carbonates), oxoacids, isopolyacids, heteropolyacids, and other inorganic compounds of the aforementioned metallic elements; salts of organic acids (e.g., acetates, propionates, hydrocyanates, naphthenates, and stearates), complexes, and other organic compounds of the metallic elements. Ligands constituting the complexes include OH (hydroxo), alkoxy (e.g., methoxy, ethoxy, propoxy, and butoxy), acyl (e.g., acetyl and propionyl), alkoxycarbonyl (e.g., methoxycarbonyl and ethoxycarbonyl), acetylacetonato, cyclopentadienyl group, halogen atoms (e.g., chlorine and bromine), CO, CN, oxygen atom, $H_2O$ (aqua), phosphines (e.g., triphenylphosphine and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Concrete examples of the metallic compounds (C1) include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids;. acetylacetonatocobalt, and other complexes, and other divalent or trivalent cobalt compounds. Illustrative vanadium compounds include vanadium hydroxide, vanadium oxide, vanadium chloride, vanadyl chloride, vanadium sulfate, vanadyl sulfate, sodium vanadate, and other inorganic compounds; acetylacetonatovanadium, vanadyl acetylacetonato, and other complexes, and other vanadium compounds having a valency of 2 to 5. Examples of compounds of the other metallic elements include compounds corresponding to the above-mentioned cobalt or vanadium compounds. Each of these metallic compounds (C1) can be used alone or in combination.

The ratio of the metallic compound (C1) to the 1,2-dicarbonyl compound or its hydroxy reductant (A) is, for example, such that the former (C1)/the latter (A) (by mole) equals about 0 to 0.1, preferably about 0.001 to 0.05, and more preferably about 0.002 to 0.02.

Of the substituents $R^1$ and $R^2$ in the imide compound (C2) represented by the formula (17), the halogen atom includes iodine, bromine, chlorine and fluorine. The alkyl group includes, but is not limited to, methyl, ethyl, propyl, isopropyl, butyl, isobutyl, s-butyl, t-butyl, hexyl, anddecyl groups, and other straight- or branched-chain alkyl groups each having about 1 to 10 carbon atoms. Preferred alkyl groups are alkyl groups each having about 1 to 6 carbon atoms, of which lower alkyl groups each having about 1 to 4 carbon atoms are particularly preferred.

The aryl group includes phenyl and naphthyl groups, for example. Illustrative cycloalkyl groups include cyclopentyl, and cyclohexyl groups. Illustrative alkoxy groups are methoxy, ethoxy, propoxy, isopropoxy, butoxy, t-butoxy, and hexyloxy groups, and other alkoxy groups each having about 1 to 10 carbor. atoms, and preferably having about 1 to 6 carbon atoms. Among them, lower alkoxy groups each having about 1 to 4 carbon atoms are especially preferred.

Examples of the alkoxycarbonyl group include methoxycarbonyl, ethoxycarbonyl, isopropoxycarbonyl, butoxycarbonyl, t-butoxycarbonyl, hexyloxycarbonyl, and other alkoxycarbonyl groups each having about 1 to 10 carbon atoms in the alkoxy moiety. Preferred carbonyl groups are alkoxycarbonyl groups each having about 1 to 6 carbon atoms in the alkoxy moiety, of which lower alkoxycarbonyl groups each having about 1 to 4 carbon atoms in the alkoxy moiety are particularly preferred. Illustrative acyl groups include, for example, formyl, acetyl, propionyl, butyryl, isobutyryl, valeryl, isovaleryl, and pivaloyl groups, and other acyl groups each having about 1 to 6 carbon atoms.

The substituents $R^1$ and $R^2$ may be identical to or different from each other. The substituents $R^1$ and $R^2$ in the formula (17) may be combined to form a double bond, or an aromatic or non-aromatic ring. The preferred aromatic or non-aromatic ring has about 5 to 12 members, and particularly about 6 to 10 members. The ring may be a heterocyclic ring or condensed heterocyclic ring, but it is often a hydrocarbon ring. Such rings include, for example, non-aromatic alicyclic rings (e.g., cyclohexane ring, and other cycloalkane rings which may have a substituent, cyclohexene ring, and other cycloalkene rings which mayhave a substituent), non-aromatic bridged rings (e.g., 5-norbornene ring, and other bridged hydrocarbon rings which may have a substituent), benzene ring, naphthalene ring, and other aromatic rings (including condensed rings) which may have a substituent. The ring is composed of an aromatic ring in many cases. The ring may have a substituent. Such substituents include, but are not limited to, alkyl groups, haloalkyl groups, hydroxyl group, alkoxy groups, carboxyl group, alkoxycarbonyl groups, acyl groups, nitro group, cyano group, amino group, and halogen atoms.

Preferred imide compounds (C2) include compounds of the following formulae:

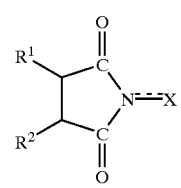

(17a)

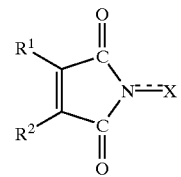

(17b)

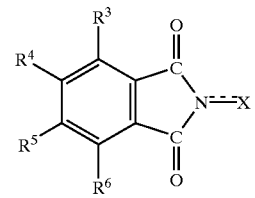

(17c)

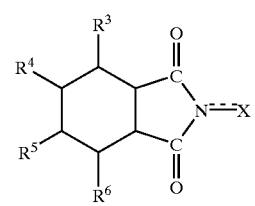

(17d)

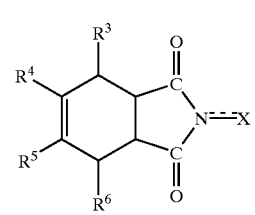

(17e)

-continued

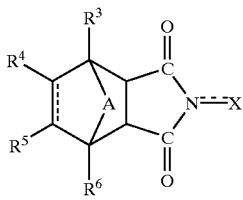

(17f)

(wherein $R^3$ to $R^6$ are each, identical to or different from one another, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom, where adjacent groups of $R^2$ to $R^6$ may be combined to form an aromatic or non-aromatic ring; A in the formula (17f) is a methylene group or an oxygen atom; and $R^1$, $R^2$ and X have the same meanings as defined above, where one or two of N-substituted cyclic imido group indicated in the formula (17c) may be further combined with the benzene ring in the formula (17c)).

In the substituents $R^3$ to $R^6$, the alkyl group includes similar alkyl groups to those exemplified above, especially alkyl groups each having about 1 to 6 carbon atoms. The haloalkyl group includes trifluoromethyl group, and other haloalkyl groups each having about 1 to 4 carbon atoms. The alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. The acyl group includes similar acyl groups to those described above, especially acyl groups each having about 1 to 6 carbon atoms. The illustrative halogen atoms include fluorine, chlorine and bromine atoms. Each of the substituents $R^3$ to $R^6$ is often a hydrogen atom, a lower alkyl group having about 1 to 4 carbon atoms, a carboxyl group, a nitro group, or a halogen atom. The ring formed together by $R^3$ to $R^6$ includes similar rings to the aforementioned rings which are formed together by $R^1$ and $R^2$. Among them, aromatic or non-aromatic 5- to 12-membered rings are partlicularly preferred.

In the formula (17), X represents an oxygen atom or a hydroxyl group, and the bond between the nitrogen atom N and X is a single bond or a double bond. Each of the imide compounds (C2) represented by the formula (17) can be used alone or in combination.

Acid anhydrides corresponding to the imide compounds (C2) represented by the formula (17) include, but are not limited to, succinic anhydride, maleic anhydride, and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Preferred imide compounds include, for example, N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimlde, N-hydroxytetrachlorophthalimide, N-hydroxychlorendimide, N-hydroxyhimimide, N-hydroxytrimellitimide, N,N'-dihydroxypyromellitlmide, and N,N'-dhydroxynaphthalenetetracarboximide. Typically preferred imide compounds include N-hydroxyimide compounds derived from alicyclic polycarboxylic anhydrides or aromatic pclycarboxylic anhydrides, of which N-hydroxyphthalimide and other N-hydroxyimide compounds derived from aromatic polycarboxylic anhydrides are especially preferred.

The imide compounds (C2) can be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

The ratio of the imide compound (C2) to the 1,2-dicarbonyl compound or its hydroxy reductant (A) is, for example, such that the former (C2)/the latter (A) (by mole) equals about 0 to 1, preferably about 0.001 to 0.5, and more preferably about 0.002 to 0.2.

The acylating agent has only to contain at least one compound selected from the metallic compounds (C1) and the imide compound (C2). Specifically, the embodiments of the acylating agent include; (i) an acylating agent composed of the 1,2-dicarbonyl compound or its hydroxy reductant (A), oxygen (B) and the metallic compound (C1), (ii) an acylating agent composed of the 1,2-dicarbonyl compound or its hydroxy reductant (A), oxygen (B) and the imide compound (C2), and (iii) an acylating agent composed of the 1,2-dicarbonyl compound or its hydroxy reductant (A), oxygen (B), the metallic compound (C1), and the imide compound (C2).

In many cases, the use of an acylating agent containing the metallic compound (C1) provides a high conversion rate, and the use of an acylating agent containing the imide compound (C2) yields an acyl group-containing compound with a high selectivity. An acylating agent containing the imide compound (C2) has a feature that when used in combination with a hydroxy reductant of the 1,2-dicarbonyl compound as the compound (A), the hydroxy reductant is immediately converted in to the corresponding 1,2-dicarbonyl compound in a system, and an acylation reaction smoothly proceeds.

The acylating agent may further comprise other components including radical generators and radical reaction accelerators, in addition to the components (A), (B) and (C). Such additional components include, for example, halogens (e.g., chlorine and bromine), peracids (e.g., peracetic acid and m-chloroperbenzoic acid), and peroxides (e.g., hydrogen peroxide and hydroperoxide).

The proportion of the 1,2-dicarbonyl compound or its hydroxy reductant (A) n the preparation of the acyl-group-containing alicyclic compound represented by the formula (4) or (5) is, for example, equal to or more than about 1 mole (about 1 to 50 moles), preferably about 1.5 to 20 moles, and more preferably about 3 to 10 moles, relative to 1 mole of the compound represented by the formula (14) or (15). The 1,2-dicarbonyl compound or its hydroxy reductant (A) can also be employed as a reaction solvent.

The proportion of the oxygen (B) is equal to or more than about 0.5 mole (e.g., equal to or more than 1 mole), preferably about 1 to 100 moles, and more preferably about 2 to 50 moles, relative to 1 mole of the compound represented by the formula (14) or (15). Excess moles of molecular oxygen relative to the compound of the formula (14) or (15) is employed in many cases.

The amount of the metallic compound (C1) is, for example, about 0.00001 to 1 mole, preferably about 0.0001 to 0.1 mole, and more preferably about 0.001 to 0.05 mole, relative to 1 mole of the compound represented by the formula (14) or (15). The proportion of the imide compound (C2) ranges, for instance, from about 0.00001 to 1 mole, preferably from about 0.001 to 0.7 mole, and more preferably from about 0.01 to 0.5 mole, relative to 1 mole of the compound represented by the formula (14) or (15).

A reaction is generally performed in an organic solvent. Such organic solvents include, but are not limited to, acetic acid, propionic acid, and other organic acids; acetonitrile, propionitrile, benzonitrile, and other nitrites; formamide, acetamide, dimethylformamide (DMF), dimethylacetamide, and other amides; t-butanol, t-amyl alcohol, and other alcohols; hexane, octane, and other aliphatic hydrocarbons; benzene, toluene, and other aromatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; diethyl ether, diisopropyl ether, and other ethers; and mixtures of these solvents. As the solvent, acetic acid or another organic acid, benzonitrile or another nitrile, trifluoromethylbenzene or another halogenated hydrocarbon is frequently employed.

A reaction temperature can be appropriately selected depending on the types of reactants, and is, for example, about 0° C. to 300° C., preferably about 30° C. to 250° C., and more preferably about 40° C. to 200° C. The reaction is often performed at a temperature of about 40° C. to 150° C. The reaction can be conducted at atmospheric pressure or under a pressure (under a load). When the reaction is conducted under a pressure, the pressure is usually about 1 to 100 atm (e.g. 1.5 to 80 atm), and preferably about 2 to 70 atm. A reaction time can be appropriately selected within a range of, for example, about 30 minutes to 48 hours depending on the reaction temperature and pressure. The reaction can be performed in a batch system, semi-batch system, continuous system or another conventional system in the presence of, or under flow of oxygen. After the completion of the reaction, reaction products can be easily separated and purified by a conventional technique such as filtration, concentration, distillation, extraction, crystallization, recrystallization, column chromatography and other separation means, or any combination of these separation means.

According to the acylation method using the acylating agent, an acyl group ($R^xCO$ group) corresponding to the 1,2-dicarbonyl compound is introduced into a junction position (bridgehead position) of the alicyclic compound represented by the formula (14) or (15). In the alicyclic compound represented by the formula (14) or (15), when $R^{c1}$ is a hydrogen atom and when $R^{d1}$ or $R^{e1}$ is a hydrogen atom, an oxidation reaction proceeds with the acylation reaction under the acylation condition, and a compound having an acyl group and a hydroxyl group respectively introduced into two junction positions may be produced.

Typical examples of the compound represented by the formula (4) or (5) include, but are not limited to, 3a-acetylperhydroindene, 3a-acetyl-7a-hydroxyperhydroindene, 3a,7a-diacetylperhydroindene, 4a-acetyldecalin, 4a-acetyl-8a-hydroxydecalin, 4a,8a-diacetyldecalin, 4a-acetylperhydrofluorene, 9a-acetylperhydrofluorene, 4a,9a-diacetylperhydrofluorene, 4a-acetylperhydroanthracene, 4a-acetyl-9a-hydroxyperhydroanthracene, 4a,9a-diacetylperhydroanthracene, 10a-acetylperhydrophenanthrene, 10a-acetyl-4a-hydroxyperhydrophenanthrene, 10a-acetyl-8a-hydroxyperhydrophenanthrene, 10a,8a-diacetylperhydrophenanthrene, 2-acetyltricyclo[5.2.1.0$^{2,6}$]decane, 2-acetyl-6-hydroxytricyclo[5.2.1.0$^{2,6}$]decane, 2,6-diacetyltricyclo[5.2.1.0$^{2,6}$]decane, 2a-acetylperhydroacenaphthene, 2a-acetyl-8a-hydroxyperhydroacenaphthene, 2a,8a-diacetylperhydroacenaphthene, 3a-acetylperhydrophenalene, 3a-acetyl-6a-hydroxyperhydrophenalene, and 3a,6a-diacetylperhydrophenalene.

The compound represented by the formula (14) or (15) for use as a material in the acylation reaction can be produced according to known techniques. For example, a compound having a hydroxyl group at a junction position (bridgehead position) can be obtained by oxidizing a corresponding compound having a hydrogen atom at the junction position with oxygen in the presence of a catalyst composed of the imide compound represented by the formula (17) or a catalyst composed of this catalyst and the metallic compound (C1). The amount of the imide compound is, for example, about 0.001 to 1 mole relative to 1 mole of the compound having a hydrogen atom at the junction position. The amount of the metallic compound (C1) is, for example, about 0.0001 to 0.7 mole relative to 1 mole of the compound having a hydrogen atom at the junction position. The oxygen is usually used in excess moles relative to the compound having a hydrogen atom at the junction position. As the oxygen, molecular oxygen can be employed. A reaction is performed at a temperature of about 0° C. to 300° C. (preferably about 30° C. to 250° C.) at atmospheric pressure or under a pressure in a solvent such as acetic acid and other organic acids, acetonitrile, benzonitrile, and other nitrites.

A compound having a carboxyl group at a junction position can be obtained by allowing a corresponding compound having a hydrogen atom at the junction position to come in contact with carbon monoxide and oxygen in the presence of a catalyst composed of the imide compound represented by the formula (17) or a catalyst composed of this catalyst and the metallic compound (C1). The amounts of the imide compound and the metallic compound (C1) are the same as in the oxidation reaction. The proportion of carbon monoxide is usually equal to or more than 1 mole (e.g., 1 to 100 moles) relative to 1 mole of the compound having a hydrogen atom at the junction position. The proportion of oxygen is equal to or more than about 0.5 mole (e.g., about 0.5 to 100 moles) relative to 1 mole of the compound having a hydrogen atom at the junction position. The ratio of carbon monoxide to oxygen is such that carbon monoxide/oxygen (by mole) equals about 1/99 to 99/1, and preferably about 10/90 to 99/1. A reaction is performed at a temperature of about 0° C. to 200° C. (preferably about 10° C. to 150° C.) at atmospheric pressure or under a pressure in a solvent such as acetic acid and other organic acids, acetonitrile, benzonitrile, and other nitrites.

A compound having a hydroxymethyl group at a junction position can be obtained by subjecting the corresponding compound having a carboxyl group at the junction position to a conventional reduction process using a reducing agent (e.g., a hydrogen-platinum group metal catalyst, sodium borohydride-Lewis acid, lithium aluminium hydride, and diborane).

A compound having a nitro group at a junction position can be obtained by allowing a corresponding compound having a hydrogen atom at the junction position to come in contact with a nitrogen oxide (e.g., $N_2O_3$, $N_2O$—$O_2$, NO—$O_2$, or $NO_2$) in the presence of, or in the absence of a catalyst composed of the imide compound represented by the formula (17). The amount of the imide compound is the same as in the oxidation reaction. The proportion of the nitrogen oxide is usually about 1 to 50 moles, and preferably about 1.5 to 30 moles, relative to 1 mole of the compound having a hydrogen atom at the junction position. A reaction is performed at a temperature of about 0° C. to 150° C. (preferably about 10° C. to 125° C.) at atmospheric pressure or under a pressure in a solvent such as acetic acid and other organic acids, acetonitrile, benzonitrile, and other nitrites.

A compound having an amino group at a junction position can be obtained by subjecting the corresponding compound having a nitro group at the junction position to a conventional reduction process using a reducing agent [e.g., hydrogen-metal catalysts (platinum group metals, nickel, and copper chromite), sodium borohydride, and diborane]. Of the compounds of the formula (14) or (15), a compound having an acyl group can be produced by using the acylation method using the acylating agent. These processes for the introduction of functional groups can also be applied to the introduction of a functional group in the invented compounds (1), (2), (10), (11) and materials compounds thereof.

Of the compounds represented by the formula (4) or (5), a compound having a methyl group as $R^x$ (an alicyclic compound having an acetyl group at a junction position) can also be obtained in the following manner. An alicyclic compound having a carboxyl group at a junction position represented by the following formula (18) or (19):

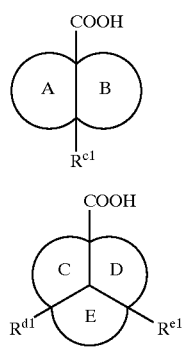

(wherein ring A, ring B, ring C, ring D, ring E, $R^{c1}$, $R^{e1}$, and $R^{e1}$ have the same meanings as defined above) is allowed to react with a halogenating agent such as thionyl chloride to yield a corresponding carboxylic acid halide derivative; the obtained carboxylic acid halide derivative is allowed to react with a Grignard reagent derived from a malonic ester such as ethyl malonate to yield a corresponding α-(adamantylcarbonyl)malonic ester; and the obtained compound is decomposed by action of an acid such as sulfuric acid.

The introduction and deprotection of a protective group in the invented compounds (1), (2), (10), and (11), and material compounds thereof can be performed according to a conventional manner (e.g., T. W. Greene, "Protective Group in Organic Synthesis", A Wiley-Interscience Publication, New York, 1981).

[Production Process of Hydroxymethyl-group-containing Alicyclic Compound (Production Process 2)]

Of the hydroxymethyl-group-containing alicyclic compounds represented by the formula (1) or (2), a compound where $R^a$ and $R^b$ are the same hydrocarbon group, i.e., the compound represented by the formula (1a) or (2a) can be obtained by the production process 2.

In the formula (1a) or (2a), hydrocarbon groups in $R^{a1}$ include the hydrocarbon groups exemplified in the substituents $R^a$ and $R^b$. Preferred $R^{a1}$ includes, for example, $C_1$–$C_{10}$ alkyl groups (typically, $C_1$–$C_6$ alkyl groups, especially $C_1$–$C_4$ alkyl groups), and 3- to 8-membered cycloalkyl groups.

In the formula (8) or (9), hydrocarbon groups which may have a substituent in $R^z$ include aliphatic hydrocarbon groups, alicyclic hydrocarbon groups, aromatic hydrocarbon groups, and groups each comprising plurality of these groups combined with each other. The substituent includes, but is not limited to, halogen atoms, substituted oxy (or thio) groups (e.g., methoxy, methylthio, methoxyethoxy, 2-(trimethylsilyl)ethoxy, and benzyloxy groups), and acyl groups (e.g., benzoyl group)

The aliphatic hydrocarbon groups include, but are not limited to, methyl, ethyl, propyl, isopropyl, butyl, isobutyl, s-butyl, t-butyl, pentyl, hexyl, octyl, decyl, vinyl, allyl, 2-propenyl, and other $C_1$–$C_{10}$ aliphatic hydrocarbon groups (alkyl groups, alkenyl groups, and alkynyl groups). Preferred aliphatic hydrocarbon groups are $C_1$–$C_6$ (especially $C_1$–$C_4$) aliphatic hydrocarbon groups. The alicyclic hydrocarbon groups include, but are not limited to, cyclopentyl, cyclohexyl, and other 3- to 8-membered alicyclic hydrocarbon groups (cycloalkyl groups and cycloalkenyl groups). The aromatic hydrocarbon groups include, for example, phenyl, naphthyl, and other $C_6$–$C_{14}$ aromatic hydrocarbon groups. The groups each comprising a plurality of different hydrocarbon groups combined with each other include,but are not limited to, benzyl, 2-phenylethyl, and other $C_7$–$C_{16}$ aralkyl groups.

Of the compounds represented by the formula (12), a compound where $R^z$ is a hydrocarbon group can be easily obtained from 1-adamantanecarboxyic acid where $R^z$ is a hydrogen atom, and a corresponding alcohol or phenol by a conventional esterification reaction using, for example, an acid catalyst.

A reaction between the compound represented by the formula (8) or (9) and the organometallic compound represented by the formula (6a) is generally performed in an inert solvent. Such solvents include, but are not limited to, diethyl ether, dibutyl ether, 1,2-dimethoxyethane, tetrahydrofuran, and other chain or cyclic ethers; hexane, heptane, octane, and other aliphatic hydrocarbons; benzene, toluene, xylene, and other aromatic hydrocarbons; cyclohexane, and other alicyclic hydrocarbons; and mixtures of these solvents. Preferred solvents include the ethers, or mixtures of the ethers with other solvents. The concentration of the ether in the solvent is preferably equal to or more than 10% by weight.

A reaction temperature can be appropriately selected depending on, for example, the type of the organometallic compound, and is generally about −100° C. to 100° C. (about 0° C. to 100° C. and preferably about 10° C. to 40° C. when an organomagnesium compound is employed). The proportion of the organometallic compound represented by the formula (6a) can be selected depending on the type of the compound and is, for example, about 2 to 4 times by equivalent (about 3 to 5 times by equivalent when $R^z$ in the formula (8) or (9) is a hydrogen atom) that of the compound of formula (8) or (9).

The reaction can be performed in a batch system, semi-batch system, continuous system, or another conventional system. When the reaction is performed in a semi-batch system, the compound of the formula (8) or (9) may be added (added dropwise) to a liquid containing the organometallic compound represented by the formula (6a), or alternatively, the organometallic compound represented by the formula (6a) may be added (added dropwise) to a liquid containing the compound of the formula (8) or (9).

After the completion of the reaction, a corresponding alicyclic compound having a 1,1-di-substituted hydroxymethyl group and represented by the formula (1a) or (2a) can be obtained by adding an aqueous solution containing an acid (e.g., hydrochloric acid, sulfuric acid and other inorganic acids; acetic acid, and other organic acids) or a salt (e.g., ammonium chloride) to a reaction mixture to decompose an adduct of the organometallic compound; adjusting the acidity or alkalinity according to necessity; and subjecting the resulting mixture to a conventional separation and purification means such as filtration, concentration, extraction, distillation, crystallization, recrystallization, or column chromatography.

As the organometallic compound represented by the formula (6a), a similar compound to the compound represented by the formula (6) can be employed.

[Polymerizable Alicyclic Compound]

In the polymerizable alicyclic compound represented by the formula (10) or (11), the ring A, ring B, ring C, ring D, ring E, $R^a$, and $R^b$ have the same meanings as defined above. Halogen atoms, alkyl groups, protective groups for hydroxyl group, protective groups for hydroxymethyl group, protective groups for amino group, protective groups for carboxyl group, and acyl groups in $R^{c2}$, $R^{d2}$, and $R^{e2}$ include, for example, the corresponding substituents exemplified in the $R^c$, $R^d$, and $R^e$.

Polycyclic carbon rings formed by the ring A and ring B in the formula (10) include, but are not limited to, perhydroindene ring, decalin ring, perhydrofluorene ring, perhydroanthracene ring, perhydrophenanthrene ring, and tricyclo[5.2.1.0$^{2,6}$]decane ring. In the formula (11), polycyclic carbon rings formed by the ring C, ring D and ring E include, for example, perhydroacenaphthene ring and perhydrophenalene ring.

Polymerizable unsaturated groups in the R include hydrocarbon groups each having a polymerizable double bond (e.g., vinyl group, isopropenyl group, allyl group, allylmethyl group, and other allyl-$C_1$–$C_4$ alkyl groups; and 2-methyl-2-propenyl group, and other α-alkyl-substituted vinyl-$C_1$–$C_4$ alkyl groups), and hydrocarbon groups each having a polymerizable triple bond (e.g., ethynyl group, 2-propynyl group, and other ethynyl-$C_1$–$C_4$ alkyl groups). Preferred polymerizable unsaturated groups each have an α,β-ethylenically unsaturated bond (e.g., vinyl group, isopropenyl group, and allyl group, especially vinyl group or isopropenyl group).

Of these polymerizable alicyclic compounds, preferred compounds include, for example, compounds where $R^{c2}$ is a hydrogen atom, compounds where $R^{d2}$ and $R^{e2}$ are hydrogen atoms, compounds where $R^{c2}$ is a hydroxyl group which may be protected by a protective group, and compounds where $R^{d2}$ and/or $R^{e2}$ is a hydroxyl group which may be protected by a protective group.

Typical examples of the polymerizable alicyclic compounds include mono- or di-acrylic esters and mono- or di-methacrylic esters corresponding to the compounds exemplified as the typical examples of the hydroxymethyl-group-containing alicyclic compounds.

[Production Process of Polymerizable Alicyclic Compound]

The polymerizable alicyclic compound represented by the formula (10) or (11) can be obtained, for example, by allowing the compound represented by the formula (1) or (2) to react with an unsaturated carboxylic acid represented by the following formula (20):

$$RCO_2H \qquad (20)$$

(wherein R has the same meaning as defined above) or a reactive derivative thereof in the presence of a catalyst composed of a compound of the Group 3 element of the Periodic Table of Elements.

Such unsaturated carboxylic acids represented by the formula (20) include compounds each having a polymerizable double bond [e.g., (meth)acrylic acid, crotonic acid, vinylacetic acid, allylacetic acid, and other monocarboxylic acids; maleic acid, fumaric acid, itaconic acid, and other polycarboxylic acids; and mono-alkyl esters of these polycarboxylic acids], and compounds each having a polymerizable triple bond (e.g., propionic acid).

Reactive derivatives of these unsaturated carboxylic acids include acid anhydrides [e.g., (meth)acrylic anhydride, and maleic anhydride], and compounds each having a leaving group (e.g., halogen atoms, alkyl groups, alkenyl groups, alkynyl groups, aryl groups, cycloalkyl groups, and aralkyl groups).

Such reactive derivatives of carboxylic acids each having a leaving group include, but are not limited to, acid halides [e.g., (meth)acrylic chloride, and (meth)acrylic bromide], alkyl esters of carboxylic acids [e.g., methyl (meth)acrylate, ethyl (meth)acrylate, propyl (meth)acrylate, butyl (meth)acrylate, isobutyl (meth)acrylate, t-butyl (meth)acrylate, and other $C_1$–$C_6$ alkyl esters of carboxylic acids (especially $C_1$–$C_4$ alkyl esters of carboxylic acids)], alkenyl esters of carboxylic acids [e.g., vinyl (meth)acrylate, allyl (meth)acrylate, 1-propenyl (meth)acrylate, isopropenyl (meth)acrylate, 1-butenyl (meth)acrylate, 2-butenyl (meth)acrylate, 3-butenyl (meth)acrylate, 2-pentenyl (meth)acrylate, and other $C_2$–$C_{10}$ alkenyl esters of carboxylic acids (especially $C_2$–$C_6$ alkenyl esters of carboxylic acids, among them, $C_2$–$C_4$ alkenyl esters of carboxylic acids)], alkynyl esters of carboxylic acids [e.g., ethynyl (meth)acrylate, propynyl (meth)acrylate, and other $C_2$–$C_{10}$ alkynyl esters of carboxylic acids (especially $C_2$–$C_6$ alkynyl esters of carboxylic acids, among them, $C_2$–$C_4$ alkynyl esters of carboxylic acids)], aryl esters of carboxylic acids [e.g., phenyl (meth)acrylate], cycloalkyl esters of carboxylic acids [e.g., cyclohexyl (meth)acrylate, and other $C_3$–$C_{10}$ cycloalkyl esters of carboxylic acids], and aralkyl esters of carboxylic acids [e.g. benzyl (meth)acrylate, and other phenyl-$C_1$–$C_4$ alkyl esters of carboxylic acids].

Preferred reactive derivatives include carboxylic acid halides, $C_1$–$C_6$ alkyl esters (especially, $C_1$–$C_4$ alkyl esters) of carboxylic acids, $C_1$–$C_6$ alkenyl esters (especially $C_2$–$C_4$ alkenyl esters) of carboxylic acids, and $C_2$–$C_6$ alkynyl esters (especially $C_2$–$C_4$ alkynyl esters) of carboxylic acids. Especially, the use of carboxylic acid halides and $C_2$–$C_6$ alkenyl esters of carboxylic acids can produce a corresponding polymerizable alicyclic compound with a high selectivity in a high yield through an exchange reaction of a leaving group while suppressing side reactions such as addition polymerization.

According to this process, the formation of, for example, amine hydrochloride can be suppressed. In addition, the use of a $C_1$–$C_4$ alkyl ester of carboxylic acid or a $C_2$–$C_4$ alkenyl ester of carboxylic acid can avoid contamination of a halogen component upon a target compound. Furthermore, a low-boiling compound (e.g., the esters) can be used as the reactant unsaturated carboxylic acid or a reactive derivative thereof, and a treatment after the reaction is easy and an isolation yield is high in this case.

The Group 3 element of the Periodic Table of Elements includes, but is not limited to, rare earth elements [e.g., scandium, yttrium, lanthanum series elements (lanthanum, cerium, praseodymium, neodymium, promethium, samarium, europium, gadolinium, terbium, dysprosium, holmium, erbium, thulium, ytterbium, and lutetium)], and actinoid series elements (e.g., actinium).

Preferred Group 3 elements of the Periodic Table of Elements include rare earth elements such as scandium, yttrium, and lanthanum series elements (e.g., samarium, gadolinium, and ytterbium). Particularly, samarium has a high catalytic activity.

In the compounds of Group 3 elements of the Periodic Table of Elements, the valency of the Group 3 element of the Periodic Table of Elements is not particularly limited and is often divalent to tetravalent, especially divalent or trivalent. The compounds of Group 3 elements of the Periodic Table of Elements are not especially limited as far as the compounds have a catalytic activity and may be metallic elementary substances, inorganic compounds (e.g., halides, oxides, complex oxides, phosphorus compounds, and nitrogen compounds), compounds with inorganic compounds (e.g., organic acids), or complexes. The compounds in question are often hydroxides or salts of oxacids, salts of organic acids, salts of inorganic acids, and halides containing the elements, or coordination compounds (complexes) containing the metallic elements. The complexes may be π-complexes such as metallocene compounds. The compounds of Group 3 elements of the Periodic Table of Elements may be complex metallic compounds with the other metals. Each of these catalysts can be used alone or in combination.

By taking samarium compounds as example, the catalytic component will be illustrated in detail below. Naturally, compounds of the other Group 3 elements of the Periodic Table of Elements corresponding to samarium compounds can also be effectively employed.

Hydroxides include, for example, samarium(II) hydroxide, and samarium(II) hydroxide. Metallic oxides include, for example, samarium(II) oxide and samarium(III) oxide.

Salts of organic acids include, but are not limited to, salts of organic acids such as organic carboxylic acids (e.g., formic acid, acetic acid, trichloroacetic acid, trifluoroacetic acid, propionic acid, butyric acid, valeric acid, naphthenic acid, stearic acid, and other monocarboxylic acids; oxalic acid, maleic acid, and other polycarboxylic acids), hydroxycarboxylic acids (e.g., glycolic acid, lactic acid, malic acid, tartaric acid, and citric acid), thiocyanic acid, and sulfonic acids (e.g., methanesulfonic acid; trichloromethanesulfonic acid, trifluoromethanesulfonic acid, ethanesulfonic acid, and other alkylsulfonic acids; and benzenesulfonic acid, p-toluenesulfonic acid, and other arylsulfonic acids). Salts of inorganic acids include, but are not limited to, nitrates, sulfates, phosphates, carbonates, and perchlorates. Illustrative organic acid salts or inorganic acid salts include, but are not limited to, samarium(III) acetate, samarium(III) acetate, samarium(II) trichloroacetate, samarium(III) trichloroacetate, samarium(II) trifluoroacetate, samarium (III) trifluoroacetate, samarium(II) trifluoromethanesulfonate (i.e., samarium(II) triflate), samarium(III) trifluoromethanesulfonate (i.e., samarium(III) triflate), samarium (II) nitrate, samarium(II) sulfate, samarium(II) phosphate, and samarium(II) carbonate.

Halides include fluorides, chlorides, bromides and iodides, such as samarium(II) iodide, samarium(III) iodide, samarium(II) bromide, samarium(III) bromide, samarium (II) chloride, and samarium(III) chloride.

Ligands constituting complexes include, but are not limited to, OH (hydroxo), methoxy, ethoxy, propoxy, andbutoxy, and other alkoxy groups, acetyl, propionyl, and other acyl groups, methoxycarbonyl (acetato), ethoxycarbonyl, and other alkoxycarbonyl groups, acetylacetonato, cyclopentadienyl, $C_1$–$C_4$ alkyl-substituted cyclopentadienyl (e.g., pentamethylcyclopentadienyl, and other $C_1$–$C_2$ alkyl-substituted cyclopentadienyl), dicyclopentadienyl, $C_1$–$C_4$ alkyl-substituted dicyclopentadienyl (e.g., pentamethyldicyclopentadienyl, and other $C_1$–$C_2$ alkyl-substituted dicyclopentadienyl), chlorine, bromine, and other halogenatoms, CO, CN, oxygenatom, $H_2O$ (aquo), phosphines (e.g., triphenylphosphine, and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds. One or more identical or different ligands may be coordinated in the complexes or complex salts.

Typical samarium complexes include, for example, bisacetylacetonatosamarium(II), trisacetylacetonatosamarium(III), biscyclopentadienylsamarium(II), triscyclopentadienylsamarium(III), bispentamethylcyclopentadienylsamarium(II trispentamethylcyclopentadienylsamarium(III), and bis($\eta^5$-pentamethylcyclopentadienyl)samarium(II).

The catalyst composed of a compound of Group 3 element of the Periodic Table of Elements may be homogenous or heterogenous. The catalyst may be a solid catalyst comprising the catalytic component composed of a compound of Group 3 element of the Periodic Table of Elements supported on a carrier. As the carrier, activated carbon, zeolite, silica, silica-alumina, bentonite, and other porous carriers are often employed. The proportion of the catalytic component in such a solid catalyst is about 0.1 to 50 parts by weight, preferably about 0.5 to 30 parts by weight, and more preferably 1 to 20 parts by weight, relative to 100 parts by weight of the carrier.

The amount of the catalyst composed of a compound of Group 3 element of the Periodic Table of Elements can be selected within a wide range, and is, for example, about 0.1 to 100% by mole, preferably about 0.5 to 50% by mole, and more preferably about 1 to 25% by mole (e.g., about 5to 20% by mole), relative to the hydroxymethyl-group-containing alicyclic compound represented by the formula (1) or (2).

The esterification reaction is advantageously performed in the presence of an oxime. The oxime can be either an aldoxime or a ketoxime. Such oximes include, for example, 2-hexanone oxime, and other aliphatic oximes, cyclohexanone oxime, and other alicyclic oximes, acetophenone oxime, benzophenone oxime, benzyl dioxime and other aromatic oximes.

The amount of the oxime can be selected within a wide range of, for example, about 0.1 to 100% by mole, preferably about 1 to 50% by mole, and more preferably about 5 to 40% by mole (e.g., about 5 to 30% by mole), relative to the hydroxymethyl-group-containing alicyclic compound represented by the formula (1) or (2).

The ratio of the unsaturated carboxylic acid represented by the formula (20) or a reactive derivative thereof to the hydroxymethyl-group-containing alicyclic compound represented by the formula (1) or (2) can be freely selected within a range not adversely affecting the production efficiency of the polymerizable alicyclic compound and is, for example, about 0.5 to 5 equivalents, preferably about 0.8 equivalent or more (e.g., about 0.8 to 5 equivalents), and typically about 1 equivalent or more (e.g., about 1 to 3 equivalents, and especially about 1 to 1.5 equivalent) relative to 1 equivalent of the hydroxymethyl-group-containing alicyclic compound. The esterification reaction is an equilibrium reaction, and the more the amount of the unsaturated carboxylic acid or a reactive derivative thereof is, the more advantageously the reaction proceeds. However, the aforementioned catalyst has a markedly high catalytic activity, and the use of the catalyst does not require large excess of the unsaturated carboxylic acid or a reactive derivative thereof. When the hydroxymethyl-group-containing alicyclic compound represented by the formula (1) or (2) has two or more hydroxyl groups, a monoester, a diester, or the like can be obtained in a high yield by appropriately selecting the amount of the unsaturated carboxylic acid represented by the formula (20) or a reactive derivative thereof.

The invented process, where the heat of reaction is low, can smoothly proceed the reaction and can yield a target compound in a high yield even if the amount of a solvent is small.

The esterification reaction can be performed in the presence of, or in the absence of an inert solvent. Such reaction solvents include, but are not limited to, hexane, octane, and other aliphatic hydrocarbons; cyclohexane, and other alicyclic hydrocarbons; benzene, toluene, xylene, and other aromatic hydrocarbons; acetone, methyl ethyl ketone, methyl isobutyl ketone, and other ketones; dioxane, diethyl ether, diisopropyl ether, tetrahydrofuran, and other ethers; dimethylformamide, dimethylacetamide, N-methylpyrrolidone, acetonitrile, benzonitrile, and other non-protonic polar solvents; and mixtures of these solvents. The unsaturated carboxylic acid or a reactive derivative thereof can be employed as a reaction solvent.

Of the hydroxymethyl-group-containing alicyclic compounds, compounds each having a plurality of hydroxyl groups have a high hydrophilicity, and are liable to form a heterogenous reaction system when a generally-employed solvent for esterification reaction (toluene and other hydrophobic solvents) is used. Accordingly, when a hydroxymethyl-group-containing alicyclic compound having a high hydrophilicity is employed, preferred solvents include hydrophilic solvents, or mixtures of hydrophilic solvents with hydrophobic solvents (aliphatic, alicyclic, or aromatic hydrocarbons). Such hydrophilic solvents include acetone, methyl ethyl ketone, and other ketones; dioxane, diethyl ether, tetrahydrofuran, and other ethers; and non-protonic polar solvents.

The reaction is an equilibrium reaction, and, in order to enhance the reaction, it is advantageous to immediately remove eliminated components or other components that adversely affect the reaction out of the reaction system. To remove the eliminated component, it is advantageous to use a high boiling solvent (e.g., an organic solvent having a boiling point of about 50° C to 120° C., typically about 60° C. to 115° C.) or an azeotropic solvent (e.g., the aforementioned hydrocarbons).

A reaction temperature in the esterification reaction can be selected within a range of, for example, about 0° C. to 150° C., and preferably about 25° C. to 120° C. The use of the catalyst composed of a compound of Group 3 element of the Periodic Table of Elements can yield the polymerizable alicyclic compound in a high yield even under mild conditions. In this case, the reaction temperature may be, for example, about 10° C. to 100° C., and preferably about 20° C. to 80° C. Especially, the use of the alkenyl ester of organic carboxylic acid or the like as the unsaturated carboxylic acid or a reactive derivative thereof can smoothly proceed the reaction even under mild conditions of about 20° C. to 50° C. The reaction can be conducted at atmospheric pressure, under a reduced pressure, or under a pressure (under a load), in a batch system, a semi-batch system, a continuous system, or another conventional system.

After the completion of the reaction, the polymerizable alicyclic compound as a reaction product can be easily separated and purified by a conventional technique such as filtration, concentration, distillation, extraction, crystallization, recrystallization, column chromatography, and other separation means, or a combination of these separation means.

The invented polymerizable alicyclic compound can be prepared by, in addition to the above process, (A) a process of allowing the hydroxymethyl-group-containing alicyclic compound represented by the formula (1) or (2) to react with the unsaturated carboxylic acid represented by the formula (20) in an appropriate solvent in the presence of an acid (e.g., hydrochloric acid, sulfuric acid, p-toluenesulfonic acid, or a cation exchange resin) at a temperature of, for example, about 0° C. to 150° C., while removing a by-produced water according to necessity, or (B) a process of allowing the hydroxymethyl-group-containing alicyclic compound represented by the formula (1) or (2) to react with a reactive derivative (e.g., an acid halide, or an acid anhydride) of the unsaturated carboxylic acid represented by the formula (20) at a temperature of, for example, about 0° C. to 100° C. in an appropriate solvent, where necessary in the presence of a base such as triethylamine or pyridine.

Of the invented polymerizable alicyclic compounds represented by the formula (10) or (11), preferred compounds, compounds where $R^{e2}$ is a hydroxyl group and compounds where $R^{d2}$ and/or $R^{e2}$ is a hydroxyl group can be obtained, for example, in the following manner.

Specifically, of the hydroxymethyl-group-containing alicyclic compounds represented by the formula (1) or (2), a dihydroxy compound (a compound having a hydroxyl group at a junction position of rings) represented by the following formula (1b) or (2b)

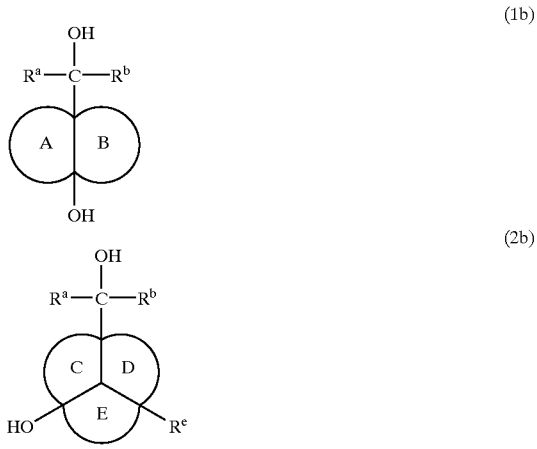

(wherein ring A, ring B, ring C, ring D, ring E, $R^a$, $R^b$, and $R^e$ have the same meaninas as defined above) is, in the same manner as described above, subjected to (i) a reaction with the unsaturated carboxylic acid represented by the formula (20) or a reactive derivative thereof in the presence of the catalyst composed of a compound of Group 3 element of the Periodic Table of Elements, to (ii) a reaction with the unsaturated carboxylic acid represented by the formula (20) in the presence of an acid, or to (iii) a reaction with a reactive derivative (e.g., an acid halide or acid anhydride) of the unsaturated carboxylic acid represented by the formula (20), where necessary in the presence of a base, to esterify both of the hydroxyl group of the hydroxymethyl group and the hydroxyl group at the junction position of rings to thereby yield a diester compound represented by the flowing formula (10a) or (11a):

(10a)

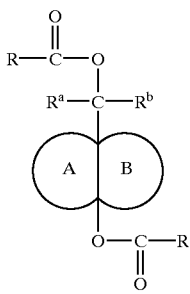

(11a)

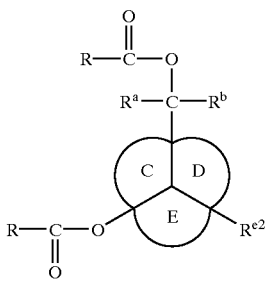

(wherein ring A, ring B, ring C, ring D, ring E, R, $R^a$, $R^b$, and $R^{e2}$ have the same meanings as defined above), and the compound represented by the formula (10a) or (11a) is partially hydrolyzed to yield a compound represented by the following formula (10b) or (11b):

(10b)

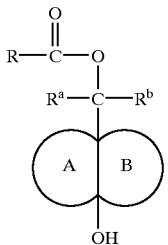

(11b)

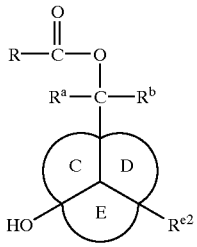

(wherein ring A, ring B, ring C, ring D, ring E, R, $R^a$, $R^b$, and $R^{e2}$ have the same meanings as defined above).

Of the above process, the esterification reaction can be performed by using 2 moles or more of the unsaturated carboxylic acid or a reactive derivative thereof relative to 1 mole of the compound represented by the formula (1b) or (2b) in the aforementioned hydrophilic solvent such as tetrahydrofuran.

The hydrolytic reaction can be performed, for example, in a non-protonic polar solvent such as dimethyl sulfoxide in the presence of an alkali such as potassium hydroxide. The proportion of the alkali is about 0.9 to 1.1 moles relative to 1 mole of the compound represented by the formula (10a) or (11a), and the proportion of water is about 0.9 to 1.5 moles relative to 1 mole of the compound represented by the formula (10a) or (11a).

According to this process, an ester group combined at a junction position of rings is selectively hydrolyzed in the hydrolysis step to yield a polymerizable alicyclic compound having a hydroxyl group at a junction position of rings in a high yield.

Other preferred polymerizable alicyclic compounds, i.e., compounds where $R^{e2}$ is a hydroxyl group protected by a protective group, and compounds where $R^{d2}$ and/or $R^{e2}$ is a hydroxyl group protected by a protective group can be obtained, for example, in the following manner.

Specifically, of the alicyclic carboxylic acid derivatives represented by the formula (8) or (9), an alicyclic carboxylic acid derivative having a hydroxyl group at a junction position and represented by the following formula (8a) or (9a):

(8a)

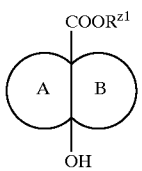

(9a)

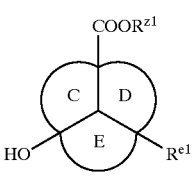

(wherein ring A, ring B, ring C, ring D, ring E, and $R^{e1}$ have the same meanings as defined above; and $R^{z1}$ is a hydrogen atom or a hydrocarbon group which may have a substituent) is subjected to a reaction for introducing a protective group to yield a compound represented by the following formula (8b) or (9b):

(8b)

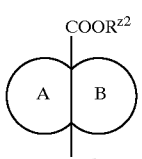

(9b)

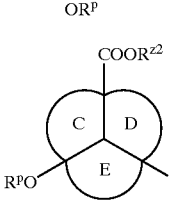

(wherein ring A, ring B, ring C, ring D, ring E, and $R^{e1}$ have the same meanings as defined above; $R^{z2}$ is a hydrogen atom or a hydrocarbon group which may have a subsistent; and $R^p$ is a protective group for hydroxyl group), this compound is then allowed to react with the organometallic compound represented by the formula (6a) to yield a compound represented by the following formula (1c) or (2c):

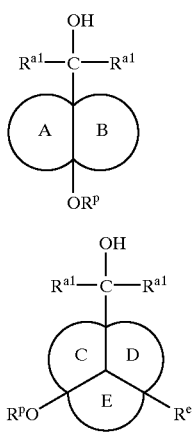

(1c)

(2c)

(wherein ring A, ring B, ring C, ring D, ring E, $R^{a1}$, $R^e$, and $R^p$ have the same meanings as defined above). This compound is then subjected, as described above, to (i) a reaction with the unsaturated carboxylic acid represented by the formula (20) or a reactive derivative thereof in the presence of the catalyst composed of a compound of Group 3 element of the Periodic Table of Elements, to (ii) a reaction with the unsaturated carboxylic acid represented by the formula (20) in the presence of an acid, or to (iii) a reaction with a reactive derivative (e.g., acid halide, or acid anhydride) of the unsaturated carboxylic acid represented by the formula (20), where necessary in the presence of a base, for esterification to yield a compound represented by the following formula (10c) or (11c):

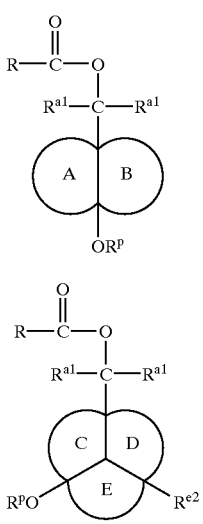

(10c)

(11c)

(wherein ring A, ring B, ring C, ring D, ring E, R, $R^{a1}$, $R^{e2}$, and $R^p$ have the same meanings as defined above).

In this process, hydrocarbon groups which may have a substituent in $R^{z1}$ in the formula (8a) or (9a) include groups similar to those in $R^z$. As the reaction for introducing a protective group into a hydroxyl group, a reaction generally used for introducing a protective group into a hydroxyl group can be applied (e.g., the aforementioned T. W. Greene, "Protective Group in Organic Synthesis", A Wiley-Interscience Publication, New York, 1981).

For example, when the hydroxyl group of the compound represented by the formula (8a) or (9a) is to be protected by methoxymethyl, methylthiomethyl, 2-methoxyethoxymethyl, 2-(trimethylsilyl)ethoxymethyl, or another substituted oxy-(or thio-)methyl group, the protective group can be introduced by allowing, for example, a substituted oxymethyl halide (e.g., a substituted oxymethyl chloride, or a substituted oxymethyl bromide) corresponding to the substituted oxymethyl group or the like to react with the compound represented by the formula (8a) or (9a), preferably in the presence of a base (e.g., trimethylamine or pyridine). To introduce an alkyl group such as methyl group as a protective group, a corresponding alkyl halide (e.g., an alkyl chloride, alkyl bromide, or alkyl iodide) is allowed to react with the compound represented by the formula (8a) or (9a) preferably in the presence of the base. Likewise, to introduce an acyl group such as acetyl group as a protective group, an acyl halide (e.g., an acyl chloride, or acyl bromide) or another acylating agent corresponding to the acyl group is allowed to react with the compound represented by the formula (8a) or (9a) preferably in the presence of the base. Thus, a desired protective group can be introduced. To introduce an acetoacetyl group as a protective group, diketene, a diketene-acetone adduct, or another acetoacetylating agent is allowed to react with the compound represented by the formula (8a) or (9a) to thereby introduce the protective group. Upon introduction of methyl group, diazomethane can also be used.

Reaction conditions in the introduction of a protective group can be appropriately selected depending on the type of the protective group. For example, a reaction temperature is for example about 0° C. to 150° C. The amount of a reagent for use in the introduction of a protective group is, for example, about 0.8 to 3 moles relative to 1 mole of the compound represented by the formula (8a) or (9a). Excess amounts of the reagent may be employed. A reaction is generally performed in an inert solvent.

A reaction product can be separated and purified by a conventional technique such as filtration, concentration, adjustment of alkalinity or acidity, extraction, crystallization, recrystallization, distillation, and column chromatography.

In the formula (8a) or (9a) thus obtained, hydrocarbon groups which may have a subsistent in $R^{z2}$ include similar groups to those in $R^z$. In this connection, when $R^z$ in the formula (8a) or (9a) is a hydrogen atom, the hydrogen atom can be converted into a protective group [e.g., 2-methoxyethoxymethyl group, and other substituted oxy- (or thio-)methyl groups] in the reaction for introducing a protective group depending on, for example, the type and amount of the protective group or the reaction temperature.

In the formula (8a) or (9a), protective groups for hydroxyl group represented by $R^p$ include the aforementioned protective groups.

In the formula (1c) or (2c), hydrocarbon groups in $R^{a1}$ are the same as mentioned above. The reaction of the compound represented by the formula (8b) or (9b) with the compound represented by the formula (6a) can be performed in the same manner as in the reaction of the compound represented by the formula (8) or (9) with the compound represented by the formula (6a).

The esterification reaction of the compound represented by the formula (1c) or (2c) can be performed, for example, by using the unsaturated carboxylic acid or a reactive derivative thereof in an amount of about 0.8 to 1.5 moles relative to 1 mole of the compound represented by the formula (1c) or (2c) in the hydrophilic solvent such as tetrahydrofuran.

According to this process, of the polymerizable alicyclic compounds represented by the formula (10) or (11), a compound having a hydroxyl group protected by a protective group at a junction position of rings where $R^a$ and $R^b$ are the same hydrocarbon groups can be easily and efficiently obtained.

In addition and advantageously, of the invented polymerizable alicyclic compounds represented by the formula (10) or (11), preferred compounds, i.e., compounds where $R^{c2}$ is a hydroxyl group, compounds where $R^{d2}$ and/or $R^{e2}$ is a hydroxyl group, compounds where $R^{c2}$ is a hydroxyl group protected by a protective group, and compounds where $R^{d2}$ and/or $R^{e2}$ is a hydroxyl group protected by a protective group can be easily and efficiently produced by the following process.

Specifically, of the acyl-group-containing alicyclic compounds represented by the formula (4) or (5), a compound having an acyl group and a hydroxyl group at junction positions of rings and represented by the following formula (4a) or (5a)

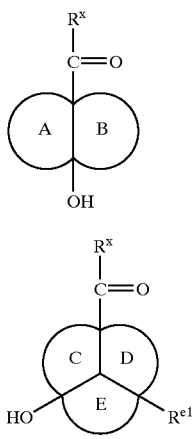

(4a)

(5a)

(wherein ring A, ring B, ring C, ring D, ring E, $R^x$, and $R^{e1}$ have the same meanings as defined above) is subjected to such a reaction for introducing a protective group as mentioned above to yield a compound represented by the following formula (4b) or (5b):

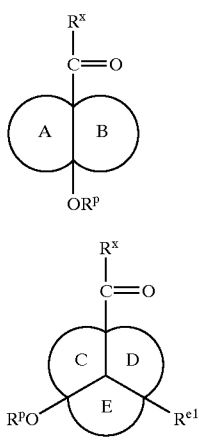

(4b)

(5b)

(wherein ring A, ring B, ring C, ring D, ring E, $R^x$, $R^{e1}$, and $R^p$ have the same meanings as defined above); this compound is then allowed to react with the organometallic compound represented by the formula (6) to yield a compound represented by the following formula (1d) or (2d):

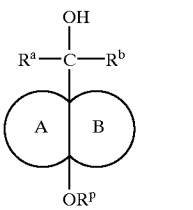

(1d)

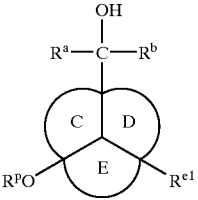

(2d)

(wherein ring A, ring B, ring C, ring D, ring E, $R^a$, $R^b$, $R^{e1}$, and $R^p$ have the same meanings as defined above); and this compound is, in the same manner as described above, subjected to (i) a reaction with the unsaturated carboxylic acid represented by the formula (20) or a reactive derivative thereof in the presence of the catalyst composed of a compound of Group 3 element of the Periodic Table of Elements, to (ii) a reaction with the unsaturated carboxylic acid represented by the formula (20) in the presence of an acid, or to (iii) a reaction with a reactive derivative (e.g., acid halide, or acid anhydride) of the unsaturated carboxylic acid represented by the formula (20), where necessary in the presence of a base, for esterification to thereby yield a compound represented by the following formula (10d) or (11d):

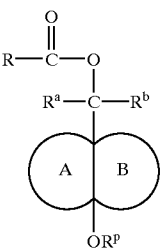

(10d)

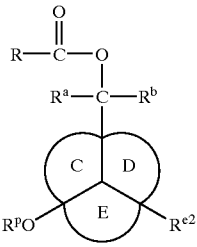

(11d)

(wherein ring A, ring B, ring C, ring D, ring E, R, $R^a$, $R^b$, $R^{e2}$, and $R^p$ have the same meanings as defined above). This compound is, of the polymerizable alicyclic compounds represented by the formula (10) or (11), a compound where $R^{c2}$ is a hydroxyl group protected by a protective group, or a compound where $R^{d2}$ and/or $R^{e2}$ is a hydroxyl group protected by a protective group.

Alternatively, the compound represented by the formula (10d) or (11d) is subjected to a reaction for eliminating a protective group (a deprotection reaction) to yield a compound represented by the following formula (10e) or (11e):

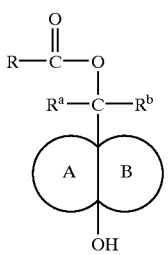
(10e)

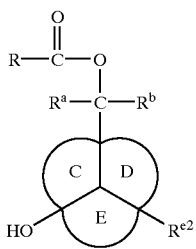
(11e)

(wherein ring A, ring B, ring C, ring D, ring E, R, $R^a$, $R^b$, and $R^{e2}$ have the same meanings as defined above). This compound is, of the polymerizable alicyclic compounds represented by the formula (10) or (11), a compound where $R^{c2}$ is a hydroxyl group, or a compound where $R^{d2}$ and/or $R^{e2}$ is a hydroxyl group.

In the above process, the compound represented by the formula (4a) or (5a) and having an acyl group and a hydroxyl group at junction positions of rings can be obtained by the aforementioned acylation method. The deprotection reaction can be performed by a conventional technique (e.g., hydrolysis or hydrogenolysis).

The invented polymerizable alicyclic compounds are thermally polymerizable or photopolymerizable in the presence of, or in the absence of a polymerization initiator (or a photopolymerization initiator). The resulting polymers thus obtained from the polymerizable alicyclic compounds are excellent in optical characteristics, mechanical characteristics, thermal properties, and electric characteristics. The polymerizable alicyclic compounds can therefore be used in a variety of applications. Such applications include, for example, optically functional materials (e.g., optical fibers and cladding materials thereof, optical elements, optical lenses, hologram, optical discs, contact lenses, and other optical materials, coating agents for organic lenses, conductive polymers, photographic sensitive materials, and fluorescent materials), coating agents (including, for example, paints), adhesives, and improvers (modifiers) for polymers.

The present invention can provide a novel alicyclic compound having a polycyclic carbon ring with two or three non-aromatic carbon rings each commonly possessing two carbon atoms, and having a 1-(mono- or di-) substituted hydroxymethyl group combined with a carbon atom at a junction position between two rings.

The invented production process can efficiently produce the above alicyclic compound in a high yield with a high selectivity.

In addition, the present invention provides a novel ester of the aforementioned alicyclic compound with a carboxylic acid having a polymerizable unsaturated group.

The present invention will be illustrated in further detail with reference to several examples below, which are not intended to limit the scope of the invention.

Preparation Example 1

A mixture of 3 mmol of cis-decalin, 18 mmol of biacetyl, 0.3 mmol of N-hydroxyphthalimide, 0.015 mmol of cobalt (II) acetate, and 3 ml of acetic acid was stirred at 75° C. in an oxygen atmosphere (1 atm) for 8 hours. A gas chromatographic analysis of products in a reaction mixture found that 4a-acetyl-cis-decalin (yield: 24%), 4a-hydroxy-cis-decalin (yield: 4%), 4a,8a-dihydroxy-cis-decalin (yield: 22%), 1,6-cyclodecanedione (yield: 10%), and 4a-acetyl-8a-hydroxy-cis-decalin (yield: 5%) were formed with a conversion rate from cis-decalin of 67%.

[Spectrum Data of 4a-Acetyl-cis-decalin]
MS m/e: 180 ([M$^+$]), 165, 137
[Spectrum Data of 4a-Acetyl-8a-hydroxy-cis-decalin]
MS m/e: 196, 178, 163, 136

Preparation Example 2

A mixture of 3 mmol of cis-syn-cis-perhydroanthracene, 18 mmol of biacetyl, 0.3 mmol of N-hydroxyphthalimide, 0.015 mmol of cobalt (II) acetate, and 3 ml of acetic acid was stirred at 75° C. in an oxygen atmosphere (1 atm) for 8 hours. A gas chromatographic analysis of products in a reaction mixture found that 4a-acetyl-cis-syn-cis-perhydroanthracene (yield: 30%), 4a-acetyl-9a-hydroxy-cis-syn-cis-perhydroanthracene (yield: 6%), 4a-hydroxy-cis-syn-cis-perhydroanthracene (yield: 8%), and 4a,9a-dihydroxy-cis-syn-cis-perhydroanthracene (yield: 5%) were formed with a conversion rate from cis-syn-cis-perhydroanthracene of 52%.

[Spectrum Data of 4a-Acetyl-cis-syn-cis-perhydroanthracene]
MS m/e: 234, 219, 190
[Spectrum Data of 4a-Acetyl-9a-hydroxy-cis-syn-cis-perhydroanthracene]
MS m/e: 250, 232, 217, 190
[Spectrum Data of 4a-Hydroxy-cis-syn-cis-perhydroanthracene]
MS m/e: 208, 190
[Spectrum Data of 4a,9a-Dihydroxy-cis-syn-cis-perhydroanthracene]
MS m/e: 224, 206, 188

Preparation Example 3

A mixture of 3 mmol of endotricyclo[5.2.1.0$^{2,6}$]decane, 18 mmol of biacetyl, 0.3 mmol of N-hydroxyphthalimide, 0.015 mmol of cobalt(II) acetate, and 3 ml of acetic acid was stirred at 75° C. in an oxygen atmosphere (1 atm) for 6 hours. A gas chromatographic analysis of products in a reaction mixture found that 2-acetylendotricyclo[5.2.1.0$^{2,6}$]decane (yield: 27%), 2-hydroxyendotricyclo[5.2.1.0$^{2,6}$]decane (yield: 11%), 2,6-dihydroxyendotricyclo[5.2.1.0$^{2,6}$]decane (yield: 16%), 2-acetyl-6-hydroxyendotricyclo[5.2.1.0$^{2,6}$]decane (yield: 6%), and dicyclo[5.2.1]decane-2,6-dione (yield: 12%) were formed with a conversion rate from endotricyclo[5.2.1.0$^{2,6}$]decane of 75%.

[Spectrum Data of 2-Acetylendotricyclo[5.2.1.0$^{2,6}$]decane]
MS m/e: 178, 163, 135
[Spectrum Data of 2-Acetyl-6-hydroxyendotricyclo[5.2.1.0$^{2,6}$]decane]
MS m/e: 194, 176, 161, 134

EXAMPLE 1

(Production of α,α-dimethyl-4a-cis-decalinmethanol)

A mixture of 0.3 mol of cis-decalin, 1.8 mol of biacetyl, 30 mmol of N-hydroxyphthalimide, 1.5 mmol of cobalt(II)

acetate, and 300 ml of acetic acid was stirred at 60° C. in an oxygen atmosphere at atmospheric pressure for 4 hours. The reaction mixture was concentrated to about 20% by weight, and was extracted with ethyl acetate, and the extract was concentrated and was then subjected to column chromatography on a silica gel to yield 4a-acetyl-cis-decalin and 4a-acetyl-8a-hydroxy-cis-decalin.

Separately, 1.1 mol of metal magnesium was placed in a flask, and the inside of the flask was replaced with nitrogen, and a solution containing 1.0 mol of bromomethane in 500 ml of THF (tetrahydrofuran) was placed in the flask in such an amount that the metal magnesium was dipped in the solution. A reaction was then initiated with a small amount of iodine, and the remainder THF solution of bromomethane was added dropwise to the mixture at such a rate that the solvent was gently refluxed. After the completion of addition, the reflux was continued for further 2 hours to yield a methylmagnesium bromide solution.

A total of 0.2 mol of 4a-acetyl-cis-decalin obtained according to the above process was dissolved in 300 ml of THF to yield a solution, and the resulting solution was added dropwise to the above methylmagnesium bromide solution at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-4a-cis-decalinmethanol represented by the following formula (yield: 54%).

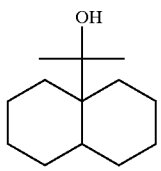

[Spectrum Data of α,α-Dimethyl-4a-cis-decalinmethanol]

MS m/e: 196, 178, 163, 137

EXAMPLE 2

[Production of 4a-(1-acryloyloxy-1-methylethyl)-cis-decalin]

A mixture of 1 mmol of α,α-dimethyl-4a-cis-decalinmethanol obtained according to Example 1, 0.1 mmol of samarium iodide (SmI$_2$), 1 mmol of isopropenyl acrylate, and 2 ml of dioxane was stirred at 50° C. for 6 hours. The reaction mixture was concentrated and was then subjected to chromatography on a silica gel to yield 4a-(1-acryloyloxy-1-methylethyl)-cis-decalin represented by the following formula (yield: 55%).

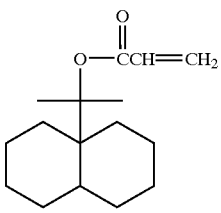

[Spectrum Data of 4a-(1-Acryloyloxy-1-methylethyl)-cis-decalin]

MS m/e: 250, 178, 163, 137

EXAMPLE 3

(Production of α,α-dimethyl-8a-hydroxy-4a-cis-decalinmethanol)

A total of 0.2 mol of 4a-acetyl-8a-hydroxy-cis-decalin obtained from cis-decalin by the process described in Example 1 was dissolved in 300 ml of THF to yield a solution. The resulting solution was added dropwise to a methylmagnesium bromide solution obtained in the same manner as in Example 1 at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-8a-hydroxy-4a-cis-decalinmethanol represented by the following formula (yield: 55%).

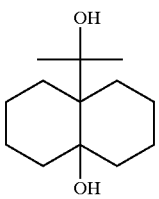

[Spectrum Data of α,α-Dimethyl-8a-hydroxy-4a-cis-decalinmethanol]

MS m/e: 212, 194, 176, 161, 135

EXAMPLE 4

[Production of 4a-(1-acryloyloxy-1-methylethyl)-8a-hydroxy-cis-decalin]

A mixture of 0.1 mol of cis-decalin, 0.5 mol of biacetyl, 10 mmol of N-hydroxyphthalimide, 1 mmol of acetylacetonatocobalt(II), and 100 ml of acetic acid was stirred at 75° C. in an oxygen atmosphere at atmospheric pressure for 4 hours. The reaction mixture was concentrated to about 20% by weight and was then extracted with ethyl acetate, and the extract was concentrated and was then washed with hexane to yield 4a-acetyl-8a-hydroxy-cis-decalin (yield: 30%). The conversion rate from cis-decalin was 68%.

A mixture of 100 mmol of 4a-acetyl-8a-hydroxy-cis-decalin, 110 mmol of 2-methoxyethoxymethyl chloride, 110 mmol of triethylamine, and 200 ml of THF was refluxed for 3 hours. The resulting reaction mixture was subjected to column chromatography on a silica gel to yield 4a-acetyl-8a-(2-methoxyethoxymethoxy)-cis-decalin represented by the following formula (yield: 90.3%). The conversion rate from 4a-acetyl-8a-hydroxy-cis-decalin was 95%.

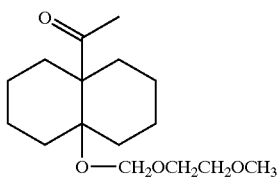

[Spectrum Data of 4a-Acetyl-8a-(2-methoxyethoxymethoxy)-cis-decalin]

MS m/e: 284, 178, 163, 134

The above-prepared 4a-acetyl-8a-(2-methoxyethoxymethoxy)-cis-decalin and methylmagnesium bromide were subjected to a reaction in the same manner as in Example 1 to yield α,α-dimethyl-8a-(2-methoxyethoxymethoxy)-4a-cis-decalinmethanol represented by the following formula (yield: 85.5%). The conversion rate from 4a-acetyl-8a-(2-methoxyethoxymethoxy)-cis-decalin was 95%.

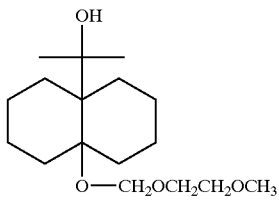

[Spectrum Data of α,α-Dimethyl-8a-(2-methoxyethoxymethoxy)-4a-cis-decalinmethanol]

MS m/e: 300, 282, 176, 161, 134

A mixture of the above-prepared α,α-dimethyl-8a-(2-methoxyethoxymethoxy)-4a-cis-decalinmethanol, 150 mmol of acrylic chloride, 150 mmol of triethylamine, and 300 ml of THF was gradually heated from room temperature up to 60° C., and was stirred at this temperature for 3 hours. The resulting reaction mixture was concentrated and was subjected to column chromatography on a silica gel to yield 4a-(1-acryloyloxy-1-methylethyl)-8a-(2-methoxyethoxymethoxy)-cis-decalin represented by the following formula (yield: 37.5%). The conversion rate from α,α-dimethyl-8a-(2-methoxyethoxymethoxy)-4a-cis-decalinmethanol was 75%.

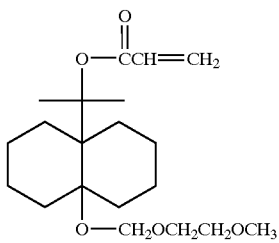

[Spectrum Data of 4a-(1-Acryloyloxy-1-methylethyl)-8a-(2-methoxyethoxymethoxy)-cis-decalin]

MS m/e: 354, 248, 176, 161, 134

A mixture of 100 mmol of 4a-(1-acryloyloxy-1-methylethyl)-8a-(2-methoxyethoxymethoxy)-cis-decalin, 6 N-hydrochloric acid (150 mmol in terms of HCl), and 30 ml of acetone was stirred at room temperature for 1 hour. The resulting reaction mixture was concentrated to yield 4a-(1-acryloyloxy-1-methylethyl)-8a-hydroxy-cis-decalin represented by the following formula (yield: 98%). The conversion rate from 4a-(1-acryloyloxy-1-methylethyl)-8a-(2-methoxyethoxymethoxy)-cis-decalin was 99%.

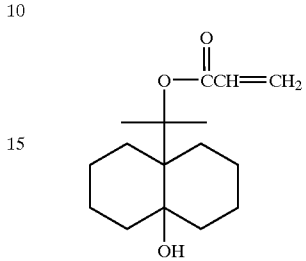

[Spectrum Data of 4a-(1-Acryloyloxy-1-methylethyl)-8a-hydroxy-cis-decalin]

MS m/e: 266, 194, 176, 161, 135

EXAMPLE 5

[Production of α,α-dimethyl-4a-cis-syn-cis-perhydroanthracenemethanol]

A mixture of 0.3 mol of cis-syn-cis-perhydroanthracene, 1.8 mol of biacetyl, 30 mmol of N-hydroxyphthalimide, 1.5 mmol of cobalt(II) acetate, and 300 ml of acetic acid was stirred at 60° C. in an oxygen atmosphere at atmospheric pressure for 4 hours. The resulting reaction mixture was concentrated to about 20% by weight, and was then extracted with ethyl acetate, and the extract was concentrated and was subjected to column chromatography on a silica gel to yield 4a-acetyl-cis-syn-cis-perhydroanthracene and 4a-acetyl-9a-hydroxy-cis-syn-cis-perhydroanthracene.

Separately, 1.1 mol of metal magnesium was placed in a flask, and the inside of the flask was-replaced with nitrogen, and a solution containing 1.0 mol of bromomethane in 500 ml. of THF (tetrahydrofuran) was placed in the flask in such an amount that the metal magnesium was dipped in the solution. A reaction was then initiated with a small amount of iodine, and the remainder THF solution of bromomethane was added dropwise to the mixture at such a rate that the solvent was gently refluxed. After the completion of addition, refluxing was continued for further 2 hours to yield a methylmagnesium bromide solution.

A total of 0.2 mole of 4a-acetyl-cis-syn-cis-perhydroanthracene obtained according to the above process was dissolved in 300 ml of THF to yield a solution, and the resulting solution was added dropwise to the above-prepared methylmagnesium bromide solution at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-4a-cis-syn-cis-perhydroanthracenemethanol represented by the following formula (yield: 42%).

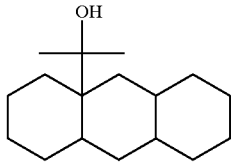

[Spectrum Data of α,α-Dimethyl-4a-cis-syn-cis-perhydroanthracenemethanol]

MS m/e: 250, 232, 217, 191

EXAMPLE 6

[Production of 4a-(1-acryloyloxy-1-methylethyl)-cis-syn-cis-perhydroanthracene]

A mixture of 1 mmol of α,α-dimethyl-4a-cis-syn-cis-perhydroanthracenemethanol obtained according to Example 5, 0.1 mmol of scandium(III) triflate, 1 mmol of vinyl acrylate, and 2 ml of dioxane was stirred at 50° C. for 6 hours. The resulting reaction mixture was concentrated and was then subjected to chromatography on a silica gel to yield 4a-(1-acryloyloxy-1-methylethyl)-cis-syn-cis-perhydroanthracene represented by the following formula (yield: 58%).

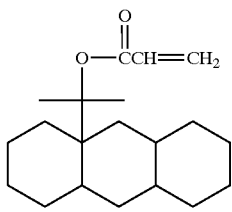

[Spectrum Data of 4a-(1-Acryloyloxy-1-methylethyl)-cis-syn-cis-perhydroanthracene]

MS m/e: 304, 232, 217, 191

EXAMPLE 7

(Production of α,α-dimethyl-9a-hydroxy-4a-cis-syn-cis-perhydroanthracenemethanol)

A total of 0.2 mol of 4a-acetyl-9a-hydroxy-cis-syn-cis-perhydroanthracene obtained from cis-syn-cis-perhydroanthracene according to the procedure described in Example 5 was dissolved in 300 ml of THF to yield a solution. The resulting solution was then added to a methylmagnesium bromide solution obtained in the same manner as in Example 1 at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-9a-hydroxy-4a-cis-syn-cis-perhydroanthracenemethanol represented by the following formula (yield: 38%).

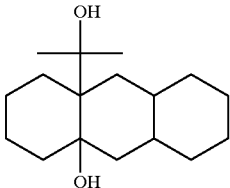

[Spectrum Data of α,α-Dimethyl-9a-hydroxy-4a-cis-syn-cis-perhydroanthracenemethanol]

MS m/e: 266, 232, 214, 199, 173

EXAMPLE 8

[Production of 4a-(1-acryloyloxy-1-methylethyl)-9a-hydroxy-cis-syn-cis-perhydroanthracene]

A mixture of 0.1 mol of cis-syn-cis-perhydroanthracene, 0.5 mol of biacetyl, 10 mmol of N-hydroxyphthalimide, 1 mmol of acetylacetonatocobalt(II), and 100 ml of acetic acid was stirred at 75° C. in an oxygen atmosphere at atmospheric pressure for 4 hours. The resulting reaction mixture was concentrated to about 20% by weight and was then extracted with ethyl acetate, and the extract was concentrated and was washed with hexane to yield 4a-acetyl-9a-hydroxy-cis-syn-cis-perhydroanthracene (yield: 26.6%). The conversion rate from cis-syn-cis-perhydroanthracene was 70%.

A mixture of 100 mmol of 4a-acetyl-9a-hydroxy-cis-syn-cis-perhydroanthracene, 110 mmol of 2-methoxyethoxymethyl chloride, 110 mmol of triethylamine, and 200 ml of THF was refluxed for 3 hours. The resulting reaction mixture was subjected to column chromatography on a silica gel to yield 4a-acetyl-9a-(2-methoxyethoxymethoxy)-cis-syn-cis-perhydroanthracene represented by the following formula (yield: 90.3%). The conversion rate from 4a-acetyl-9a-hydroxy-cis-syn-cis-perhydroanthracene was 95%.

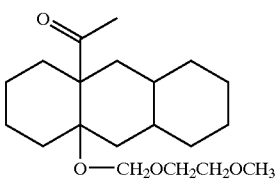

[Spectrum Data of 4a-Acetyl-9a-(2-methoxyethoxymethoxy)-cis-syn-cis-perhydroanthracene]

MS m/e: 338, 232, 217, 188

The above-prepared 4a-acetyl-9a-(2-methoxyethoxymethoxy)-cis-syn-cis-perhydroanthracene and methylmagnesium bromide were subjected to a reaction in the same manner as in Example 1 to yield α,α-dimethyl-9a-(2-methoxyethoxymethoxy)-4a-cis-syn-cis-perhydroanthracenemethanol represented by the following formula (yield: 87.4%). The conversion rate from 4a-acetyl-9a-(2-methoxyethoxymethoxy)-cis-syn-cis-perhydroanthracene was 95%.

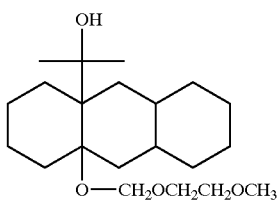

[Spectrum Data of α,α-Dimethyl-9a-(2-methoxyethoxymethoxy)-4a-cis-syn-cis-perhydroanthracenemethanol]

MS m/e: 354, 336, 230, 215, 188

A mixture of the above-prepared α,α-dimethyl-9a-(2-methoxyethoxymethoxy)-4a-cis-syn-cis-perhydroanthracenemethanol, 150 mmol of acrylic chloride, 150 mmol of triethylamine, and 300 ml of THF was gradually heated from room temperature up to 60° C., and was stirred at this temperature for 3 hours. The resulting reaction mixture was concentrated and was subjected to column chromatography on a silica gel to yield 4a-(1-acryloyloxy-1-methylethyl)-9a-(2-methoxyethoxymethoxy)-cis-syn-cis-perhydroanthracene represented by the following formula (yield: 42.4%). The conversion rate from α,α-dimethyl-9a-(2-methoxyethoxymethoxy)-4a-cis-syn-cis-perhydroanthracenemethanol was 80%.

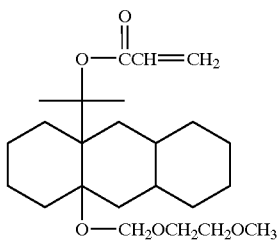

[Spectrum Data of 4a-(1-Acryloyloxy-1-methylethyl)-9a-(2-methoxyethoxymethoxy)-cis-syn-cis-perhydroanthracene]

MS m/e: 408, 302, 230, 215, 188

A mixture of 100 mmol of 4a-(1-acryloyloxy-1-methylethyl)-9a-(2-methoxyethoxymethoxy)-cis-syn-cis-perhydroanthracene, 6 N-hydrochloric acid (150 mmol in terms of HCl), and 30 ml of acetone was stirred at room temperature for 1 hour. The resulting reaction mixture was concentrated to yield 4a-(1-acryloyloxy-1-methylethyl)-9a-hydroxy-cis-syn-cis-perhydroanthraene represented by the following formula (yield: 98%). The conversion rate from 4a-(1-acryloyloxy-1-methylethyl)-9a-(2-methoxyethoxymethoxy)-cis-syn-cis-perhydroanthracene was 99%.

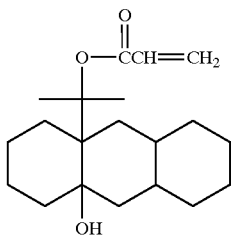

[Spectrum Data of 4a-(1-Acryloyloxy-1-methylethyl)-9a-hydroxy-cis-syn-cis-perhydroanthracene]

MS m/e: 320, 302, 230, 215, 188

EXAMPLE 9

(Production of α,α-dimethyl-2-endotricyclo [5.2.1.0$^{2,6}$] decanemethanol)

A mixture of 0.3 mol of endotricyclo[5.2.1.0$^{2,6}$]decane, 1.8 mol of biacetyl, 30 mmol of N-hydroxyphthalimide, 1.5 mmol of cobalt(II) acetate, and 300 ml of acetic acid was stirred at 60° C. in an oxygen atmosphere at atmospheric pressure for 4 hours. The resulting reaction mixture was concentrated to about 20% by weight and was then extracted with ethyl acetate, and the extract was concentrated and was subjected to column chromatography on a silica gel to yield 2-acetylendotricyclo[5.2.1.0$^{2,6}$]decane and 2-acetyl-6-hydroxyendotricyclo[5.2.1.0$^{2,6}$]decane.

Separately, 1.1 mol of metal magnesium was placed in a flask, and the inside of the flask was replaced with nitrogen, and a solution containing 1.0 mol of bromomethane in 500 ml of THF was placed in the flask in such an amount that the metal magnesium was dipped in the solution. A reaction was then initiated with a small amount of iodine, and the remainder THF solution of bromomethane was added dropwise to the mixture at such a rate that the solvent was gently refluxed. After the completion of addition, the reflux was continued for further 2 hours to yield a methylmagnesium bromide solution.

A total of 0.2 mol of 2-acetylendotricyclo[5.2.1.0$^{2,6}$] decane obtained according to the above process was dissolved in 300 ml of THF to yield a solution, and the resulting solution was added dropwise to the above-prepared methylmagnesium bromide solution at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-2-endotricyclo[5.2.1.0$^{2,6}$] decanemethanol represented by the following formula (yield: 47%).

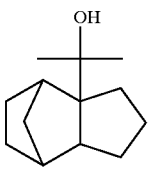

[Spectrum Data of α,α-Dimethyl-2-endotricyclo[5.2.1.0$^{2,6}$]decanemethanol]

MS m/e: 194, 176, 161, 135

EXAMPLE 10

[Production of 4a-(1-acryloyloxy-1-methylethyl)-endotricyclo[5.2.1.0$^{2,6}$]decane]

A mixture of 1 mmol of α,α-dimethyl-2-endotricyclo [5.2.1.0$^{2,6}$]decanemethanol obtained according to Example 9, 1.5 mmol of acrylic chloride, 1.5 mmol of triethylamine, and 3 ml of THF was stirred at 60° C. for 3 hours. The resulting reaction mixture was subjected to column chromatography on a silica gel to yield 4a-(1-acryloyloxy-1-methylethyl)-endotricyclo[5.2.1.0$^{2,6}$]decane represented by the following formula (yield: 52%).

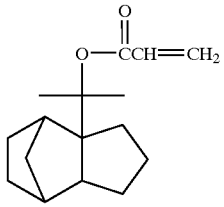

[Spectrum Data of 4a-(1-Acryloyloxy-1-methylethyl)-endotricyclo[5.2.1.0$^{2,6}$]decane]

MS m/e: 248, 176, 161, 135

EXAMPLE 11

(Production of α,α-dimethyl-6-hydroxy-2-endotricyclo[5.2.1.0$^{2,6}$]decanemethanol)

A total of 0.2 mol of 2-acetyl-6-hydroxyendotricyclo [5.2.1.0$^{2,6}$]decane cobtained from endotricyclo[5.2.1.0$^{2,6}$]decane according to the process described in Example 9 was dissolved in 300 ml of THF to yield a solution. The resulting solution was added dropwise to a methylmagnesium bromide solution obtained in the same manner as in Example 1 at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-6-hydroxy-2-endotricyclo[5.2.1.0$^{2,6}$]decanemethanol represented by the following formula (yield: 46%)

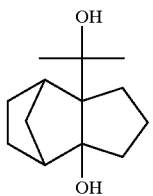

[Spectrum Data of α,α-Dimethyl-6-hydroxy-2-endotricyclo[5.2.1.0$^{2,6}$]decanemethanol]

MS m/e: 210, 192, 174, 159, 133

EXAMPLE 12

[Production of 2-(1-acryloyloxy-1-methylethyl)-6-hydroxy-endotricyclo[5.2.1.0$^{2,6}$]decane]

A mixture of 0.1 mol of endotricyclo[5.2.1.0$^{2,6}$]decane, 0.5 mol of biacetyl, 10 mmol of N-hydroxyphthalimide, 1 mmol of acetylacetonatocobalt(II), and 100 ml of acetic acid was stirred at 75° C. in an oxygen atmosphere at atmospheric pressure for 4 hours. The resulting reaction mixture was concentrated to about 20% by weight and was then extracted with ethyl acetate, was dried, and was washed with hexane to yield 2-acetyl-6-hydroxyendotricyclo[5.2.1.0$^{2,6}$] decane (yield: 27.8%). The conversion rate from endotricyclo[5.2.1.0$^{2,6}$]decane was 75%.

A mixture of 100 mmol of 2-acetyl-6-hydroxyendotricyclo[5.2.1.0$^{2,6}$]decane, 110 mmol of 2-methoxyethoxymethyl chloride, 110 mmol of triethylamine, and 200 ml of THF was refluxed for 3 hours. The resulting reaction mixture was concentrated, and was subjected to column chromatography on a silica gel to yield 2-acetyl-6-(2-methoxyethoxymethoxy)endotricyclo [5.2.1.0$^{2,6}$]decane represented by the following formula (yield: 90.3%). The conversion rate from 2-acetyl-6-hydroxyendotricyclo[5.2.1.0$^{2,6}$]decane was 95%.

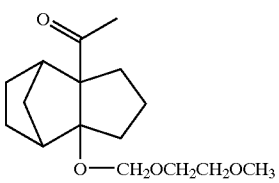

[Spectrum Data of 2-Acetyl-6-(2-methoxyethoxymethoxy)endotricyclo[5.2.1.0$^{2,6}$]decane]

MS m/e: 282, 176, 161, 132

The above-prepared 2-acetyl-6-(2-methoxyethoxymethoxy)endotricyclo[5.2.1.0$^{2,6}$]decane and methylmagnesium bromide were subjected to a reaction according to the process described in Example 1 to yield α,α-dimethyl-6-(2-methoxyethoxymethoxy)-2-endotricyclo [5.2.1.0$^{2,6}$]decanemethanol represented by the following formula (yield 85.5%), The conversion rate from 2-acetyl-6-(2-methoxyethoxymethoxy)endotricyclo[5.2.1.0$^{2,6}$] decane was 95%.

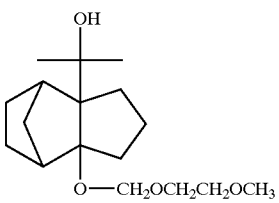

[Spectrum Data of α,α-Dimethyl-6-(2-methoxyethoxymethoxy)-2-endotricyclo [5.2.1.0$^{2,6}$] decanemethanol]

MS m/e: 298, 280, 174, 159, 132

A mixture of the above-prepared α,α-dimethyl-6-(2-methoxyethoxymethoxy)-2-endotricyclo[5.2.1.0$^{2,6}$] decanemethanol, 150 mmol of acrylic chloride, 150 mmol of triethylamine, and 300 ml of THF was gradually heated from room temperature up to 60° C. and was stirred at this temperature for 3 hours. The resulting reaction mixture was concentrated and was subjected to chromatography on a silica gel to yield 2-(1-acryloyloxy-1-methylethyl)-6-(2-methoxyethoxymethoxy)endotricyclo[5.2.1.0$^{2,6}$]decane represented by the following formula (yield: 43.9%). The conversion rate from α,α-dimethyl-6-(2-methoxyethoxymethoxy)-2-endotricyclo[5.2.1.0.$^{2,6}$] decanemethanol was 77%.

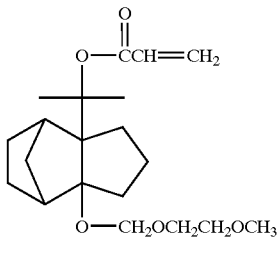

[Spectrum Data of 2-(1-Acryloyloxy-1-methylethyl)-6-(2-methoxyethoxymethoxy)endotricyclo[5.2.1.0$^{2,6}$]decane]

MS m/e: 352, 246, 174, 159, 132

A mixture of 100 mmol of 2-(1-acryloyloxy-1methylethyl)-6-(2-methoxyethoxymethoxy)endotricyclo[5.2.1.0$^{2,6}$]decane, 6 N-hydrochloric acid (150 mmol in terms of HCl), and 30 ml of acetone was stirred at room temperature for 1 hour. The resulting reaction mixture was concentrated to yield 2-(1-acryloyloxy-1-methylethyl)-6-hydroxy-endotricyclo[5.2.1.0$^{2,6}$]decane represented by the following formula (yield: 98%). The conversion rate from 2-(1-acryloyloxy-1-methylethyl)-6-(2-methoxyethoxymethoxy)endotricyclo[5.2.1.0$^{2,6}$]decane was 99%.

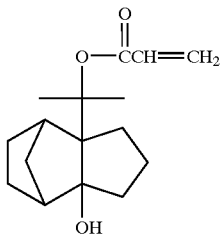

[Spectrum Data of 2-(1-Acryloyloxy-1-methylethyl)-6-hydroxy-endotricyclo[5.2.1.0$^{2,6}$]decane]

MS m/e: 264, 246, 174, 159, 132

EXAMPLE 13

[Production of 8a-acetyloxy-4a-(1-acryloyloxy-1-methylethyl)-cis-decalin]

A mixture of 100 mmol of 4a-(1-acryloyloxy-1-methylethyl)-8a-hydroxy-cis-decalin obtained in the same manner as in Example 4, 110 mmol of acetyl chloride, 110 mmol of triethylamine, and 300 ml of tetrahydrofuran was refluxed for 4 hours. The resulting reaction mixture was subjected to column chromatography on a silica gel to yield 8a-acetyloxy-4a-(1-acryloyloxy-1-methylethyl)-cis-decalin represented by the following formula (yield: 89.1%). The conversion rate from 4a-(1-acryloyloxy-1-methylethyl)-8a-hydroxy-cis-decalin was 99%.

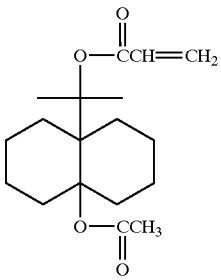

[Spectrum Data of 8a-Acetyloxy-4a-(1-acryloyloxy-1-methylethyl)-cis-decalin]

MS m/e: 308, 248, 176, 161, 134

EXAMPLE 14

[Production of 8a-acetoacetyloxy-4a-(1-acryloyloxy-1-methylethyl)-cis-decalin]

A mixture of 100 mmol of 4a-(1-acryloyloxy-1-methylethyl)-8a-hydroxy-cis-decalin prepared in the same manner as in Example 4, 110 mmol of diketene, 110 mmol of triethylamine, and 300 ml of tetrahydrofuran was stirred at room temperature for 2 hours. The resulting reaction mixture was subjected to chromatography on a silica gel to yield 8a-acetoacetyloxy-4a-(1-acryloyloxy-1-methylethyl)-cis-decalin represented by the following formula (yield: 89.1%). The conversion rate from 4a-(1-acryloyloxy-1-methylethyl)-8a-hydroxy-cis-decalin was 99%.

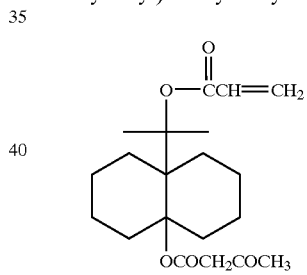

[Spectrum Data of 8a-Acetoacetyloxy-4a-(1-acryloyloxy-1-methylethyl)-cis-decalin]

MS m/e: 350, 248, 176, 161, 134

EXAMPLE 15

[Production of 9a-acetyloxy-4a-(1-acryloyloxy-1-methylethyl)-cis-syn-cis-perhydroanthracene]

A mixture of 100 mmol of 4a-(1-acryloyloxy-1-methylethyl)-9a-hydroxy-cis-syn-cis-perhydroanthracene prepared in the same manner as in Example 8, 110 mmol of acetyl chloride, 110 mmol of triethylamine, and 300 ml of tetrahydrofuran was refluxed for 4 hours. The resulting reaction mixture was subjected to chromatography on a silica gel to yield 9a-acetyloxy-4a-(1-acryloyloxy-1-methylethyl)-cis-syn-cis-perhydroanthracene represented by the following formula (yield: 91.1%). The conversion rate from 4a-(1-acryloyloxy-1-methylethyl)-9a-hydroxy-cis-syn-cis-perhydroanthracene was 99%.

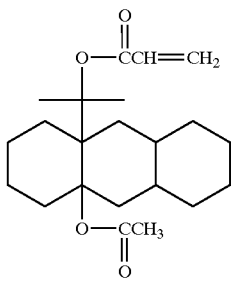

[Spectrum Data of 9a-Acetyloxy-4a-(1-acryloyloxy-1-methylethyl)-cis-syn-cis-perhydroanthracene]

MS m/e: 362, 302, 230, 215, 188

EXAMPLE 16

[Production of 9a-acetoacetyloxy-4a-(1-acryloyloxy-1-methylethyl)-cis-syn-cis-perhydroanthracene]

A mixture of 100 mmol of 4a-(1-acryloyloxy-1-methylethyl)-9a-hydroxy-cis-syn-cis-perhydroanthracene prepared in the same manner as in Example 8, 110 mmol of diketene, 110 mmol of triethylamine, and 300 ml of tetrahydrofuran was stirred at room temperature for 2 hours. The resulting reaction mixture was subjected to chromatography on a silica gel to yield 9a-acetoacetyloxy-4a-(1-acryloyloxy-1-methylethyl)-cis-syn-cis-perhydroanthracene represented by the following formula (yield: 91.1%). The conversion rate from 4a-(1-acryloyloxy-1-methyl-ethyl)-9a-hydroxy-cis-syn-cis-perhydroanthracene was 99%.

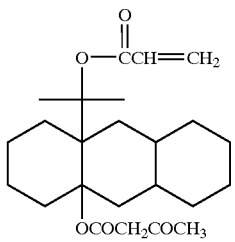

[Spectrum Data of 9a-Acetoacetyloxy-4a-(1-acryloyloxy-1-methylethyl)-cis-syn-cis-perhydroanthracene]

MS m/e: 404, 302, 230, 215, 188

EXAMPLE 17

[Production of 6-acetyloxy-2-(1-acryloyloxy-1-methylethyl)endotricyclo[5.2.1.0$^{2,6}$]decane]

A mixture of 100 mmol of 2-(1-acryloyloxy-1-methylethyl)-6-hydroxy-endotricyclo[5.2.1.0$^{2,6}$]decane prepared in the same manner as in Example 12, 110 mmol of acetyl chloride, 110 mmol of triethylamine, and 300 ml of tetrahydrofuran was refluxed for 4 hours. The resulting reaction mixture was subjected to chromatography on a silica gel to yield 6-acetyloxy-2-(1-acryloyloxy-1-methylethyl)endotricyclo[5.2.1.0$^{2,6}$]decane represented by the following formula (yield: 89.1%). The conversion rate from 2-(1-acryloyloxy-1-methylethyl)-6-hydroxy-endotricyclo[5.2.1.0$^{2,6}$]decane was 99%.

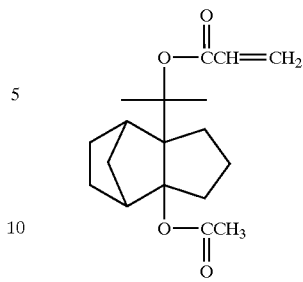

[Spectrum Data of 6-Acetyloxy-2-(1-acryloyloxy-1-methylethyl)endotricyclo[5.2.1.0$^{2,6}$]decane]

MS m/e: 308, 248, 176, 161, 134

EXAMPLE 18

[Production of 6-acetoacetyloxy-2-(1-acryloyloxy-1-methylethyl)endotricyclo[5.2.1.0$^{2,6}$]decane]

A mixture of 100 mmol of 2-(1-acryloyloxy-1-methylethyl)-6-hydroxy-endotricyclo[5.2.1.0$^{2,6}$]decane prepared in the same manner as in Example 12, 110 mmol of diketene, 110 mmol of triethylamine, and 300 ml of tetrahydrofuran was stirred at room temperature for 2 hours. The resulting reaction mixture was subjected to chromatography on a silica gel to yield 6-acetoacetyloxy-2-(1-acryloyloxy-1-methylethyl)endotricyclo[5.2.1.0$^{2,6}$]decane represented by the following formula (yield: 90.1%). The conversion rate from 2-(1-acryloyloxy-1-methylethyl)-6-hydroxy-endotricyclo[5.2.1.0$^{2,6}$]decane was 99%.

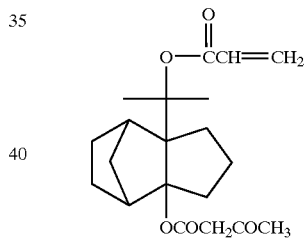

[Spectrum Data of 6-Acetoacetyloxy-2-(1-acryloyloxy-1-methylethyl)endotricyclo[5.2.1.0$^{2,6}$]decane]

MS m/e: 350, 248, 176, 161, 134

EXAMPLE 19

(Production of α,α-dimethyl-6-hydroxy-2-endotricyclo[5.2.1.0$^{2,6}$]decanemethanol)

A mixture of 0.3 mol of 2-carboxy-6-hydroxyendotricyclo[5.2.1.0$^{2,6}$]decane, 0.45 mol of n-butanol, 15 mmol of sulfuric acid, and 900 ml of toluene was stirred under reflux for 5 hours. The resulting reaction mixture was concentrated and was then subjected to column chromatography on a silica gel to yield 2-butoxycarbonyl-6-hydroxyendotricyclo[5.2.1.0$^{2,6}$]decane in a yield of 85.6%. The conversion rate from 2-carboxy-6-hydroxyendotricyclo[5.2.1.0$^{2,6}$]decane was 92%.

A total of 0.2 mol of the above-prepared 2-butoxycarbonyl-6-hydroxyendotricyclo[5.2.1.0$^{2,6}$]decane was dissolved in 300 ml of THF to yield a solution, and the resulting solution was added dropwise to a methylmagnesium bromide solution obtained in the same manner as in Example 1 at such a rate that the solvent was gently refluxed. The reflux was continued for further 2 hours after the completion of addition. The resulting reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with two portions of 500 ml of diethyl ether; the organic layer was added to the extract, and the resulting mixture was concentrated; and the concentrate was cooled and was crystallized to yield α,α-dimethyl-6-hydroxy-2-endotricyclo[5.2.1.0$^{2,6}$]decanemethanol (yield: 67%). The conversion rate from 2-butoxycarbonyl-6-hydroxyendotricyclo[5.2.1.0$^{2,6}$]decane was 83%.

What is claimed is:

1. A polymerizable alicyclic compound represented by the following formula (10) or (11):

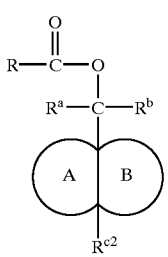

(10)

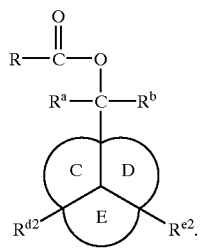

(11)

2. A polymerizable alicyclic compound according to claim 1, wherein each of said ring A, ring B, ring C, ring D, and ring E is a cyclopentane ring, a cyclohexane ring, or a bridged ring.

3. A polymerizable alicyclic compound according to claim 1, wherein a polycyclic carbon ring formed by the ring A and ring B, or by the ring C, ring D and ring E in the formula (10). or (11) is a perhydroindene ring, a decalin ring, a perhydrofluorene ring, a perhydroanthracene ring, a perhydrophenanthrene ring, a tricyclo[5.2.1.0$^{2,6}$]decane ring, a perhydroacenaphthene ring, or a perhydrophenalene ring.

4. A polymerizable alicyclic compound according to one of claims 1 to 3, wherein R is a vinyl group, an isopropenyl group, or an allyl group.

* * * * *